(12) United States Patent
Mackiewicz

(10) Patent No.: US 8,236,039 B2
(45) Date of Patent: Aug. 7, 2012

(54) VENA CAVA FILTER HAVING WALL CONTACTS

(75) Inventor: David Mackiewicz, Scotts Valley, CA (US)

(73) Assignee: Abbott Laboratories, Abbott Park, IL (US)

( * ) Notice: Subject to any disclaimer, the term of this patent is extended or adjusted under 35 U.S.C. 154(b) by 292 days.

(21) Appl. No.: 12/338,980

(22) Filed: Dec. 18, 2008

(65) Prior Publication Data

US 2009/0187210 A1    Jul. 23, 2009

Related U.S. Application Data

(60) Provisional application No. 61/016,273, filed on Dec. 21, 2007, provisional application No. 61/016,266, filed on Dec. 21, 2007.

(51) Int. Cl.
   *A61F 2/06* (2006.01)
(52) U.S. Cl. ........................................................ 623/1.1
(58) Field of Classification Search .................. 606/191, 606/192, 194, 198, 200; 623/1.13, 1.14, 623/1.24, 1.1, 1.12, 1.15, 1.16, 1.18, 1.19, 623/1.2, 1.21
   See application file for complete search history.

(56) References Cited

U.S. PATENT DOCUMENTS

| | | | |
|---|---|---|---|
| 4,733,665 A | 3/1988 | Palmaz | |
| 5,087,244 A | 2/1992 | Wolinsky et al. | |
| 5,545,208 A | 8/1996 | Wolff et al. | |
| 5,549,635 A | 8/1996 | Solar | |
| 5,690,644 A | 11/1997 | Yurek et al. | |
| 5,728,068 A | 3/1998 | Leone et al. | |
| 5,776,140 A | 7/1998 | Cottone | |
| 5,782,839 A * | 7/1998 | Hart et al. ...................... | 606/113 |
| 5,836,965 A | 11/1998 | Jendersee et al. | |
| 5,860,966 A | 1/1999 | Tower | |
| 5,871,468 A | 2/1999 | Kramer et al. | |
| 5,920,975 A | 7/1999 | Morales | |
| 5,976,181 A | 11/1999 | Whelan et al. | |
| 5,980,530 A | 11/1999 | Willard et al. | |
| 6,074,381 A | 6/2000 | Dinh et al. | |

(Continued)

FOREIGN PATENT DOCUMENTS

DE       19509464       6/1996

(Continued)

OTHER PUBLICATIONS

U.S. Appl. No. 61/016,266, filed Dec. 21, 2007, Mackiewicz.

(Continued)

*Primary Examiner* — Ryan Severson
*Assistant Examiner* — Jonathan W Miles
(74) *Attorney, Agent, or Firm* — Workman Nydegger; Jonathan D. Feuchtwang

(57) ABSTRACT

The present invention is a luminal filter having wall contacts. The filter is formed to include: a plurality of filter elements interconnected so as to form a filter body shaped in a free recovery form and having a plurality of apertures disposed between and defined by the interconnected filter elements. The apertures are dimensioned so as to inhibit a thrombus of a selected size from passing through the apertures and being dimensioned so as to allow blood components smaller than the selected size to pass through the apertures. The polymeric wall contact is coupled to the filter and disposed on an external surface thereof. Optionally, a fastener can be used to secure the wall contact to the filter.

20 Claims, 5 Drawing Sheets

U.S. PATENT DOCUMENTS

| | | | |
|---|---|---|---|
| 6,082,990 | A | 7/2000 | Jackson et al. |
| 6,106,530 | A | 8/2000 | Harada |
| 6,110,180 | A | 8/2000 | Foreman et al. |
| 6,120,522 | A | 9/2000 | Vrba et al. |
| 6,264,683 | B1 | 7/2001 | Stack et al. |
| 6,267,776 | B1 * | 7/2001 | O'Connell ............... 606/200 |
| 6,280,412 | B1 | 8/2001 | Pederson, Jr. et al. |
| 6,296,655 | B1 | 10/2001 | Gaudoin et al. |
| 6,352,547 | B1 | 3/2002 | Brown et al. |
| 6,481,262 | B2 | 11/2002 | Ching et al. |
| 6,510,722 | B1 | 1/2003 | Ching et al. |
| 6,517,559 | B1 * | 2/2003 | O'Connell ............... 606/158 |
| 6,769,161 | B2 | 8/2004 | Brown et al. |
| 6,863,683 | B2 | 3/2005 | Schwager et al. |
| 7,347,869 | B2 * | 3/2008 | Hojeibane et al. ........ 623/1.24 |
| 2002/0007207 | A1 | 1/2002 | Shin et al. |
| 2002/0068967 | A1 * | 6/2002 | Drasler et al. ........... 623/1.13 |
| 2003/0097172 | A1 | 5/2003 | Shalev et al. |
| 2003/0208227 | A1 | 11/2003 | Thomas |
| 2003/0212450 | A1 | 11/2003 | Schlick |
| 2004/0073155 | A1 | 4/2004 | Laufer et al. |
| 2005/0096735 | A1 * | 5/2005 | Hojeibane et al. ........ 623/1.24 |
| 2005/0143752 | A1 | 6/2005 | Schwager et al. |
| 2005/0203606 | A1 | 9/2005 | VanCamp |
| 2006/0030923 | A1 | 2/2006 | Gunderson |
| 2006/0041271 | A1 | 2/2006 | Bosma et al. |
| 2007/0208370 | A1 | 9/2007 | Hauser et al. |
| 2008/0208118 | A1 | 8/2008 | Goldman |
| 2009/0105747 | A1 | 4/2009 | Chanduszko et al. |
| 2009/0187211 | A1 | 7/2009 | Mackiewicz |
| 2010/0152765 | A1 | 6/2010 | Haley |
| 2011/0106234 | A1 | 5/2011 | Grandt |

FOREIGN PATENT DOCUMENTS

| | | |
|---|---|---|
| EP | 0716836 | 6/1996 |
| EP | 1637177 | 5/2004 |
| EP | 2322118 | 11/2009 |
| WO | WO 99/16382 | 4/1999 |
| WO | WO 00/78249 | 12/2000 |
| WO | WO 01/05462 | 1/2001 |
| WO | WO 01/21110 | 3/2001 |
| WO | WO 2007/061927 | 5/2007 |
| WO | WO 2008/024491 | 2/2008 |
| WO | WO 2008/024621 | 2/2008 |
| WO | WO 2009/066330 | 5/2009 |
| WO | WO2009/086205 | 7/2009 |
| WO | WO 2011/050979 | 5/2011 |

OTHER PUBLICATIONS

U.S. Appl. No. 12/338,981, Aug. 2, 2010, Restriction Requirement.
U.S. Appl. No. 12/338,981, Oct. 27, 2010, Office Action.
U.S. Appl. No. 12/609,513, Mar. 12, 2012, Office Action.
U.S. Appl. No. 13/151,893, filed Jun. 2, 2011, Mackiewicz.
U.S. Appl. No. 12/338,981, Mar. 2, 2011, Office Action.
U.S. Appl. No. 13/151,893, Jan. 27, 2012, Office Action.
U.S. Appl. No. 61/138,455, filed Dec. 17, 2008, Haley.
U.S. Appl. No. 12/537,097, Dec. 15, 2011, Restriction Requirement.
U.S. Appl. No. 12/537,097, Feb. 3, 2012, Office Action.
U.S. Appl. No. 13/502,084, filed Oct. 29, 2010, Grandt.
U.S. Appl. No. 09/957,216, mailed Jun. 10, 2003, Restriction Requirement.
U.S. Appl. No. 09/957,216, mailed Sep. 26, 2003, Office Action.
U.S. Appl. No. 09/957,216, mailed Jun. 14, 2004, Office Action.
U.S. Appl. No. 09/957,216, mailed Nov. 4, 2004, Notice of Allowance.
U.S. Appl. No. 09/957,216, mailed Feb. 16, 2005, Issue Notification.
U.S. Appl. No. 11/064,692, mailed Feb. 21, 2008, Office Action.
U.S. Appl. No. 11/064,692, mailed Oct. 14, 2008, Office Action.
U.S. Appl. No. 11/064,692, mailed Mar. 31, 2009, Office Action.
U.S. Appl. No. 11/064,692, mailed Nov. 23, 2009, Office Action.
U.S. Appl. No. 11/064,692, mailed Mar. 29, 2011, Office Action.
U.S. Appl. No. 11/064,692, mailed Aug. 2, 2011, Office Action.
U.S. Appl No. 13/151,893, mailed Apr. 3, 2012, Office Action.

* cited by examiner

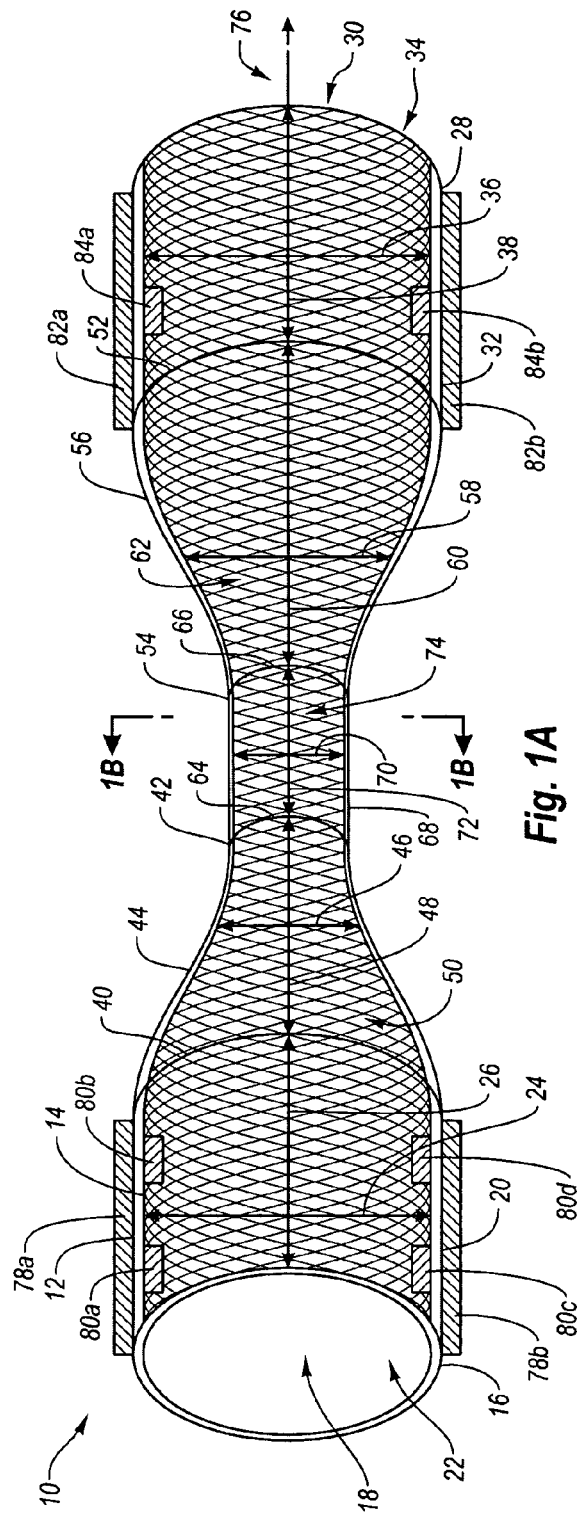
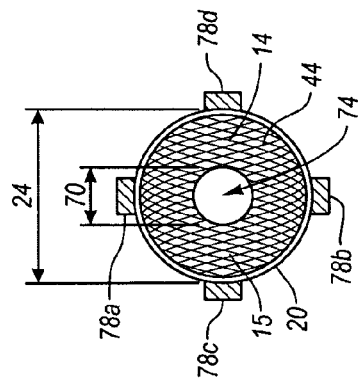

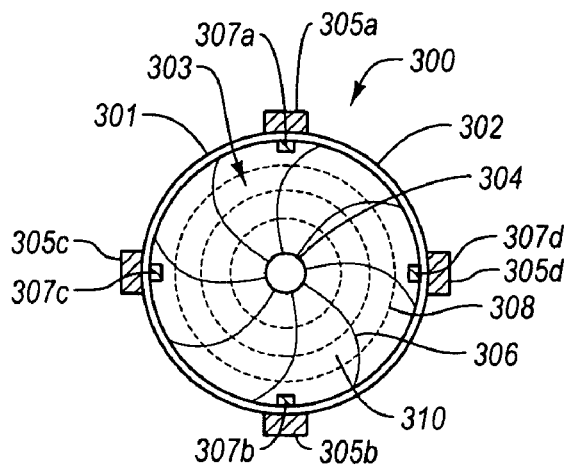
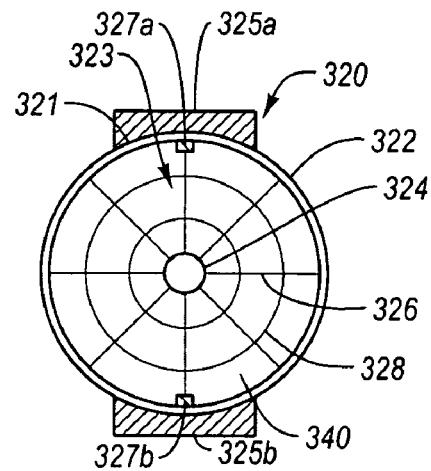
*Fig. 3A*  *Fig. 3B*
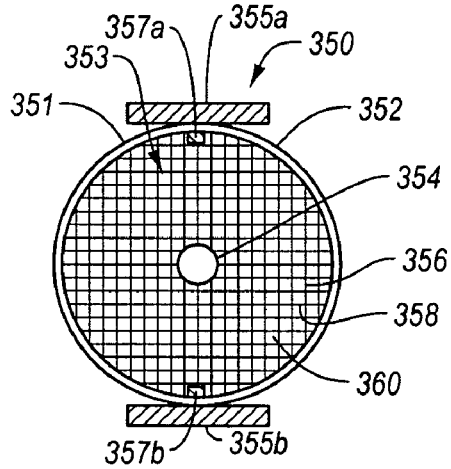
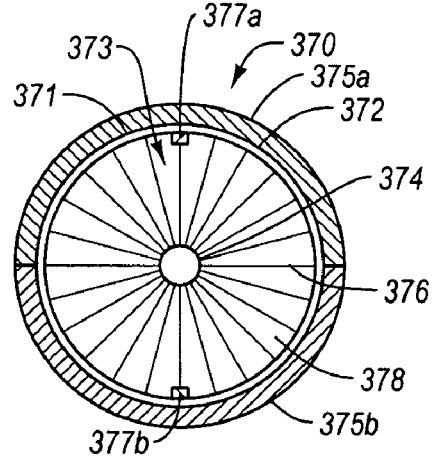
*Fig. 3C*  *Fig. 3D*
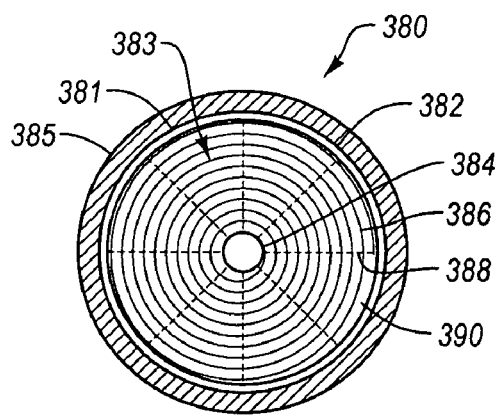
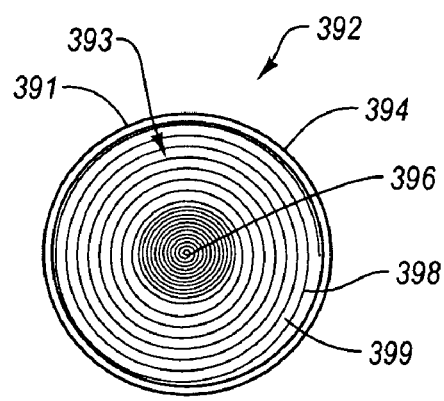
*Fig. 3E*  *Fig. 3F*

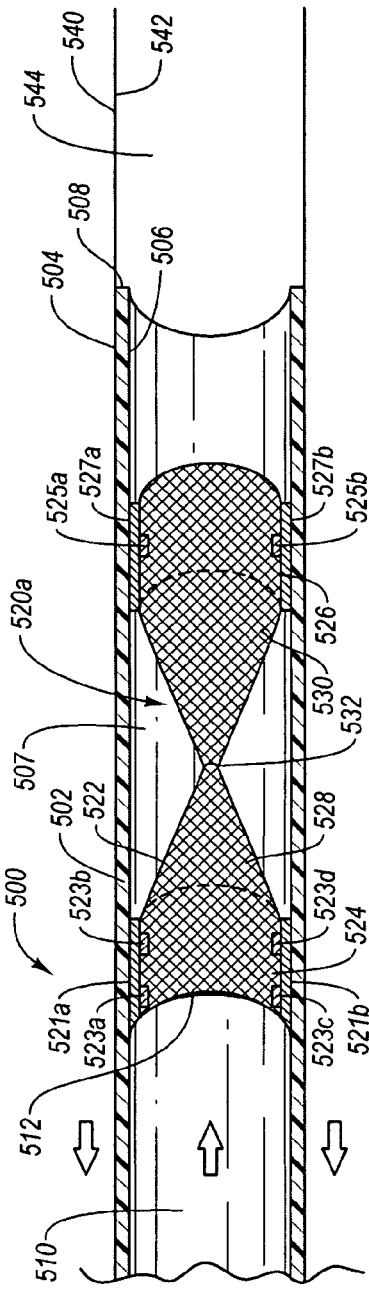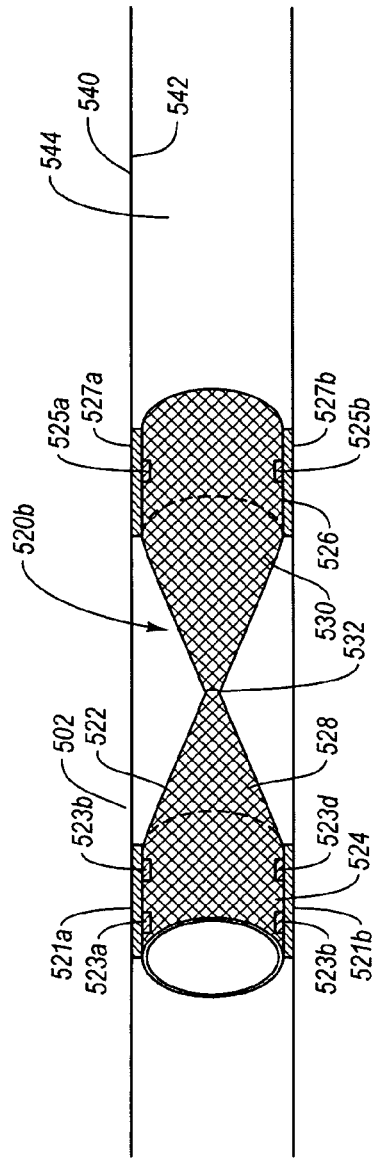
Fig. 5A
Fig. 5B

VENA CAVA FILTER HAVING WALL CONTACTS

CROSS-REFERENCE TO RELATED APPLICATIONS

This application claims the benefit of and priority to U.S. Provisional Patent Application No. 61/016,273 filed Dec. 21, 2007, and entitled "Vena Cava Filter Having Hourglass Shape" and U.S. Provisional Patent Application No. 61/016,266 filed Dec. 21, 2007, and entitled "Vena Cava Filter Having Wall Contacts", each of which is incorporated herein by reference in its entirety.

BACKGROUND OF THE INVENTION

1. The Field of the Invention

The present invention relates to a filter for use in a body lumen, such as the vena cava. More particularly, the present invention relates to a lumen filter that has wall contacts.

2. Background

Vein thrombosis is a medical condition wherein a blood clot, or thrombus, has formed inside a vein. Such a clot often develops in the calves, legs, or lower abdomen, but can also affect other veins in the body. The clot may partially or completely block blood flow, and may break off and travel through the bloodstream. Commonly, the clot is caused by a pooling of blood in the vein, often when an individual is bed-ridden for an abnormally long duration of time, for example, when resting following surgery or suffering from a debilitating illness, such as a heart attack or traumatic injury. However, there are many other situations that cause the formation of a blood clot.

Vein thrombosis is a serious problem because of the danger that the clot may break off and travel through the bloodstream to the lungs, causing a pulmonary embolism. This is substantially a blockage of the blood supply to the lungs that causes severe hypoxia and cardiac failure, and frequently results in death. For many patients, anti-coagulant drug therapies may be sufficient to dissipate the clots. For example, patients may be treated with anticoagulants such as heparin and with thrombolytic agents such as streptokinase.

Unfortunately, some patients may not respond to such drug therapy or may not tolerate such therapy. Also, there may be other reasons why an anticoagulant is not desirable. For example, patients may have an acute sensitivity to heparin or may suffer from prolonged internal and/or external bleeding as a result of such drug therapies. Also, such drug therapies simply may be ineffective in preventing recurrent pulmonary emboli. In such circumstances, surgical procedures are required to prevent pulmonary emboli. Methods for prevention of primary or recurrent pulmonary emboli when anticoagulation therapies are ineffective are well-defined in the prior art. The current standard of therapy for prevention of pulmonary emboli in patients who are classified high-risk or are unable to be anticoagulated is percutaneous insertion and placement of an inferior vena cava filter device.

Additionally, a pulmonary embolism is an obstruction of the pulmonary artery or one of its branches by a blood clot or other foreign substance. A pulmonary embolism can be caused by a blood clot which migrated into the pulmonary artery or one of its branches. Mechanical interruption of the inferior vena cava presents an effective method of preventing of pulmonary embolisms.

Vena cava filters are devices which are implanted in the inferior vena cava, providing a mechanical barrier to undesirable particulates. The filters are used to filter peripheral venous blood clots and other particulates, which if remaining in the blood stream can migrate in the pulmonary artery or one of its branches and cause harm.

Conventional implantable blood filters employing a variety of geometries are known. Many are generally basket shaped, in order to provide adequate clot-trapping area while permitting sufficient blood flow. Also known are filters formed of various loops of wire, including some designed to partially deform the vessel wall in which they are implanted. A detailed discussion of the construction and use of such filters is contained in U.S. Pat. No. 5,893,869 issued to Barnhart, which is incorporated herein by reference. Additional information on such filters can also be found in an article entitled "Percutaneous Devices for Vena Cava Filtration" by Daniel E. Walsh and Michael Bettmann contained in Current Therapy in Vascular Surgery (3d ed. 1995) at pages 945-949; this article is also incorporated herein by reference.

Along with their many functional shapes, conventional filters may include other features. For example, peripheral arms may be provided to perform a centering function so that a filter is accurately axially aligned with the vessel in which it is implanted. In order to prevent migration under the pressure induced by normal circulation, many filters have anchoring features. Such anchoring features may include hook or ridges.

Many presently used vena cava filters are permanently implanted in the inferior vena cava and remain there for the duration of the patient's life or are removably implanted, but still which remain in position for long durations. As such, the filters can incur tissue ingrowth from the surrounding tissue, resulting in a decreased blood flow and in blood clots. While some permanent filters are designed to be percutaneously retrievable, they often become embedded as their anchoring features become endothelialized by the vessel wall and retrieval must be done surgically.

BRIEF SUMMARY OF THE INVENTION

The present invention provides a filter for use in a body lumen. For example, as the filter can be a vena cava filter. More particularly, the present invention provides a lumen filter that has wall contacts (e.g., biodegradable polymer) that separate the filter from the inner surface of the body lumen so as to inhibit endothelial cell ingrowth into the lumen filter.

In one embodiment, the present invention provides a filter having a wall contact for use in a body lumen of a subject. Such a filter includes: a plurality of filter elements interconnected so as to form a filter body having a plurality of apertures disposed between and defined by the interconnected filter elements, the apertures extending from an external surface to an internal surface of the filter body and being dimensioned so as to inhibit a thrombus of a selected size from passing through the apertures and being dimensioned so as to allow blood components smaller than the selected size to pass through the apertures; and at least one biodegradable wall contact coupled to at least one of the filter elements on the external surface of the filter body, the wall contact having an initial thickness dimension that is substantially orthogonal to central axis of the filter body and that separates the external surface from an inner wall of the body lumen.

In one embodiment, the present invention provides a filter having a removable wall contact for use in a body lumen of a subject. Such a filter includes: a plurality of filter elements interconnected so as to form a filter body having a plurality of apertures disposed between and defined by the interconnected filter elements, the apertures extending from an external surface to an internal surface of the filter body and being dimensioned so as to inhibit a thrombus of a selected size from passing through the apertures and being dimensioned so as to allow blood components smaller than the selected size to pass through the apertures; at least one filter element defining at least one fastener hole extending from the external surface to the internal surface; at least one fastener extending through the at least one fastener hole; and at least one biodegradable wall contact removably coupled to the at least one filter element on the external surface of the filter body by being coupled to the at least one fastener extending through the at least one fastener hole, the wall contact having an initial thickness dimension that is substantially orthogonal to central axis of the filter body and that separates the external surface from an inner wall of the body lumen.

In one embodiment, the filter body has at least one of the following: substantially a funnel shape with a conduit having a larger end opposite of a smaller end, said smaller end being dimensioned so as to inhibit a thrombus of a selected size from passing therethrough; substantially a cone shape with a cavity having a larger end opposite of an apex to inhibit a thrombus of a selected size from passing therethrough; or substantially an hourglass shape with a conduit having a narrow median portion being dimensioned so as to inhibit a thrombus of a selected size from passing therethrough.

In one embodiment, the wall contact further includes at least one of the following: a square to rectangular block cross section; a square to rectangular block cross section having a long dimension that extends from the external surface of the filter body; a square to rectangular block cross section having a concave surface coupled to the external surface of the filter body; a square to rectangular block cross section having a concave surface coupled to the external surface of the filter body and an opposite convex surface configured to conform with the inner wall of the body lumen; an opposite convex surface configured to conform with the inner wall of the body lumen; or an arc-shaped cross section having a concave surface coupled to the external surface of the filter body and extending around at least ¼ of a circumference of the external surface of the filter body, and having an opposite convex surface configured to conform with the inner wall of the body lumen.

In one embodiment, at least one wall contact has a longitudinal length dimensioned to inhibit the filter from migrating within the body lumen of the subject. As such, the longitudinal length of the wall contact has a dimension from about 0 (or 0.0001 millimeters) to about 10 millimeters, or any size therebetween.

In one embodiment, the wall contact is dimensioned so as to inhibit endothelial cell ingrowth into the apertures.

In one embodiment, the filter includes at least one of the following: the wall contact being coated onto the external surface so as to extend into at least a portion of the plurality of apertures; a filter element defining a hole with a portion of the wall contact extending therethrough; a filter element defining a hole with a fastener extending therethrough and coupling with the at least one wall contact; a filter element defining a hole shaped as a keyway slot and a portion of the wall contact extending therethrough; a filter element defining a hole shaped as a keyway slot with a fastener extending therethrough and coupling with the at least one wall contact; a filter element defining a hole shaped as a keyway slot having a large portion and a narrow portion and a portion of the wall contact extending therethrough, the portion of the wall contact having a stem that fits through the narrow portion of the keyway slot and a head portion that fits through the large portion and that is larger than the narrow portion of the keyway slot; or a filter element defining a hole shaped as a keyway slot having a large portion and a narrow portion with a fastener extending therethrough and coupling with the at least one wall contact, the fastener having a stem that fits through the narrow portion of the keyway slot and a head portion that fits through the large portion and that is larger than the narrow portion of the keyway slot.

In one embodiment, the wall contact is formed from a biodegradable polymer selected from the group consisting of a natural polymer, synthetic polymer, polysaccharide, starch, cellulose, protein, gelatin, casein, polyesters, polyhydroxyalkanoates, lignin, shellac, natural rubber, polyalkylene esters, polylactic acids, polylactides, polyglycolic acids, polyglycolides, polyamide esters, polyvinyl esters, polyvinyl alcohols, polyanhydrides, polyesters, salts thereof, copolymers thereof, and combinations thereof.

In one embodiment, the present invention provides a method of manufacturing a filter having a wall contact for use in a body lumen of a subject. Such a method includes: forming a filter body including a plurality of filter elements interconnected together such that the filter body has a plurality of apertures disposed between and defined by the interconnected filter elements, the apertures extending from an external surface to an internal surface of the filter body and being dimensioned so as to inhibit a thrombus of a selected size from passing through the apertures and being dimensioned so as to allow blood components smaller than the selected size to pass through the apertures; forming at least one fastener hole in the filter body so as to extend from the external surface to the internal surface; inserting at least one fastener extending through the at least one fastener hole; and coupling at least one biodegradable wall contact to the external surface of the filter body by being coupled to the at least one fastener extending through the at least one fastener hole, the wall contact having an initial thickness dimension that is substantially orthogonal to central axis of the filter body and that separates the external surface from an inner wall of the body lumen.

In one embodiment, the method of manufacture includes at least one of the following: forming the wall contact so as to have a square to rectangular block cross section; forming the wall contact so as to have a square to rectangular block cross section having a long dimension that extends from the external surface of the filter body; forming the wall contact so as to have a square to rectangular block cross section having a convex surface coupled to the external surface of the filter body; forming the wall contact so as to have a square to rectangular block cross section having a concave surface coupled to the external surface of the filter body and an opposite convex surface configured to conform with the inner wall of the body lumen; forming the wall contact so as to have an arc-shaped cross section having a concave surface coupled to the external surface of the filter body and an opposite convex surface configured to conform with the inner wall of the body lumen; or forming the wall contact so as to have an arc-shaped cross section having a concave surface coupled to the external surface of the filter body and extending around at least ¼ of a circumference of the external surface of the filter body, and having an opposite convex surface configured to conform with the inner wall of the body lumen.

In one embodiment, the method of manufacture further includes forming the wall contact so as to have a longitudinal length dimensioned to inhibit the filter from migrating within the body lumen of the subject.

In one embodiment, the method of manufacture further includes: forming the at least one fastener hole shaped as a keyway slot having a large portion and a narrow portion; and forming the at least one fastener to have a stem that fits through the narrow portion of the keyway slot and a head portion that fits through the large portion and that is larger than the narrow portion of the keyway slot.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings. Moreover, the features of the drawings are not drawn to scale it is understood that one of ordinary skill in the arts would understand the appropriate size and size-relatedness of the various features shown in the figures.

FIG. 1A is a schematic representation illustrating a side view of an embodiment of a filter having wall contacts.

FIG. 1B is a cross-sectional view of the filter of FIG. 1A.

FIGS. 3A-3F are schematic representations illustrating cross-sectional profiles for embodiments of filters having wall contacts.

FIG. 5A is a schematic representation illustrating a cutaway view of an embodiment of a delivery system delivering an embodiment of the filter into a body lumen.

FIG. 5B is a schematic representation illustrating a cutaway view of the filter of FIG. 5A after being deployed within the body lumen.

DETAILED DESCRIPTION

Figure 2A:
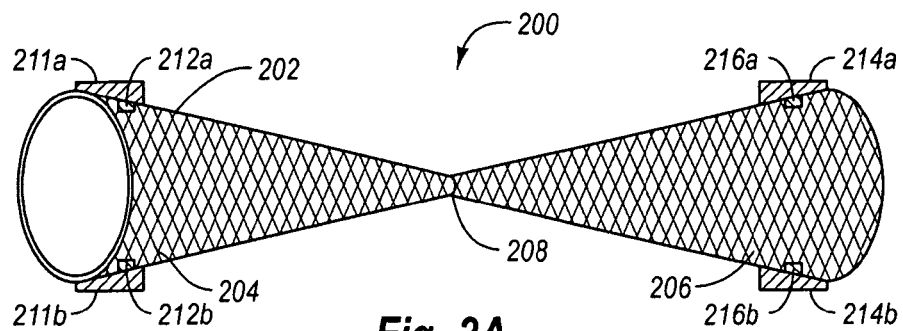
FIGS. 2A-2D are schematic representations illustrating side views of embodiments of filters having wall contacts.

The present invention provides a filter for use in a body lumen, such a lumen filter can be configured as a vena cava filter. More particularly, the present invention provides a lumen filter that has wall contacts (e.g., biodegradable polymer) that separate the filter from the inner surface of the body lumen so as to inhibit endothelial cell ingrowth into the lumen filter. Optionally, the lumen filter has substantially an hourglass shape or other substantially symmetrical shape about a central point that is formed by being laser cut from a tube or braided and then formed into the free recovery shape so as to longitudinally elongate and radially collapse during delivery or retrieval and to longitudinally shorten and radially expand after being set. Optionally, the filter is substantially half of the hourglass shape so as to be conical or funnel shaped. The substantially hourglass shape, conical shape, and/or funnel shape can be referred to as a free recovery shape because it allows for the body to longitudinally elongate and radially collapse during delivery or retrieval and to longitudinally shorten and radially expand after being set. Thus, the free recovery shape allows for easy delivery and provides for the possibility of retrieval.

I. Introduction

Accordingly, the present invention is a filter that is implantable in a blood vessel or other lumen in the body of the patient. Such filters may utilize one or more members arranged to capture particulates within the blood flow, without substantially interfering with the normal blood flow. Such a filter can be formed from a shape memory material for implantation into a vessel and subsequent extraction therefrom. The filter has wall contacts (e.g., biodegradable polymer) that separate the filter from the inner surface of the body lumen. The vascular filter captures particulates (e.g. thrombus) within the blood flow in the vessel, and retains such particulates during extraction. Prior to implantation, the filter is generally longitudinally elongated and radially collapsed. The filter can be delivered with a delivery device that is compatible or includes a catheter. After being inserted to the place of deployment, the filter reverts to a predetermined shape that is suitable for filtering the blood flow by radially expanding and longitudinally shortening.

The predetermined shape of the filter includes a plurality of interconnected members that are disposed about a longitudinal axis and that form a conical shape, funnel shape, bi-conical shape, or hourglass shape in order to provide the free recovery shape. The bi-conical shape or hourglass shape can be described as two funnels or funnels coupled at their respective tips or a portion of each funnel or funnel proximal of a tip or central axis, which can include the bottom aperture of two conical members being joined so that a conduit of appropriate size extends therethrough. When referred to as funnels, the filter includes two funnels coupled together at or near their small openings.

In one embodiment, the filter of the present invention is a vena cava filter. The vena cava filter can be implantable in the inferior vena cava, and is utilized to filter peripheral venous blood clots, a thrombus, and/or other appropriately sized particulates. The filter can be permanently or removably implanted, which is facilitated by the wall contacts that separate the filter from the inner surface of the body lumen. While the free recovery design allows for a more readily extractable filter, the filter is also suitable for long-term or permanent implantation. Accordingly, the filter can be configured to be deployed at the aortic arch of the aorta providing cerebral embolic protection. The filter can be positioned in the base of the aortic arch, between the aortic valve and the brachiocephalic artery. Any potential emboli are captured by the filter, thereby preventing entry into the neurovasculature. However, the filter of the present invention can be positioned at any suitable portion of the vena cava, or even configured for deployment in a non-vasculature lumen such as the urethra.

In one embodiment, multiple filters of the present invention can be employed. For example, a first filter can be positioned in the brachiocephalic artery and a second filter can be positioned in the left common carotid artery of the aortic arch. Any potential emboli are thereby captured by the filters so as to prevent entry into the neurovasculature.

In one embodiment, the present invention is a filter for use in a body lumen of a subject. Such a filter includes a plurality of filter elements interconnected so as to form a filter body having a plurality of apertures disposed between and defined by the interconnected filter elements. The apertures are dimensioned so as to inhibit a thrombus of a selected size from passing through the apertures and are dimensioned so as to allow blood components smaller than the selected size to pass through the apertures. At least one wall contact (e.g., biodegradable polymer) is disposed on the filter body so as to separate the filter from the inner surface of the body lumen and to anchor the filter in place. In one embodiment, the filter body includes a first funnel having a first funnel-shaped body defining a first conduit having a first larger end fluidly coupled to and opposite of a first smaller end. The first funnel-shaped body has a plurality of first apertures defined by the interconnected filter elements.

In one embodiment, the filter body includes a second funnel having a second funnel-shaped body defining a second conduit having a second larger end fluidly coupled to and opposite of a second smaller end. The second funnel-shaped body has a plurality of second apertures defined by the interconnected filter elements. The second smaller end of the second funnel is fluidly coupled to the first smaller end of the first funnel, the first smaller end and second smaller end are dimensioned so as to inhibit a thrombus of a selected size from passing therethrough.

In one embodiment, the luminal filter includes a median portion having a median body defining a median conduit having a first end coupled to the first smaller end of the first funnel and having a second end coupled to the second smaller end of the second funnel. The median conduit being dimensioned so as to inhibit a thrombus of a selected size from passing through the median conduit.

In one embodiment, the lumen filter body is configured such that the first larger end of the first funnel and/or the second larger end of the second funnel each have a reduced dimension when tensile longitudinal forces are applied to the filter body. Also, the filter body is configured such that the first larger end of the first funnel and/or the second larger end of the second funnel each have an enlarged dimension when compressive longitudinal forces are applied to the filter body.

In one embodiment, the filter body further includes at least one of the following: a first tube having a first tube-shaped body defining a first tube conduit and having a first end fluidly coupled to the first larger end of the first funnel-shaped body, said first tube having a first length; or a second tube having a second tube-shaped body defining a second tube conduit and having a second end fluidly coupled to the second larger end of the second funnel-shaped body, said second tube having a second length. The first length of the first tube and/or the second length of the second tube can be dimensioned to inhibit the filter from migrating within the body lumen of the subject. This can include at least one of the first length or second length having a dimension from about 0 millimeters (or 0.0001 mm) to about 10 millimeters, or any size therebetween.

In one embodiment, the first funnel is shaped to trap the thrombus of the selected size within the respective conduit at a central axial position and to allow removal of the thrombus when the filter is removed. The filter body has sufficient rigidity to reconfigure the body lumen from an oblong-shaped cross section to a circular-shaped cross section. The interconnected filter elements are formed from laser shaping the filter body. The interconnected filter elements are formed from braids.

In one embodiment, the present invention provides a method of utilizing a luminal filter in a body lumen of a subject. Such a method includes the following: providing a luminal filter as described herein; longitudinally elongating the filter body such that the large ends of the filter have a reduced dimension; delivering the elongated filter body to a desired deployment site within the body lumen of the subject; and longitudinally shortening the filter body such that the large ends of the filter each have an enlarged dimension that applies radial forces to an inner wall of the body lumen through the wall contacts.

In one embodiment, such a method can optionally further include: longitudinally elongating the filter body such that the larger ends filter have a reduced dimension with a cross section that is smaller than the body lumen; and retrieving the elongated filter body from the desired deployment site within the body lumen of the subject.

In one embodiment, at least one of delivering or retrieving the filter is performed with a catheter.

II. Lumen Filter

Generally, the filter of the present invention includes a filter body disposed about a longitudinal axis. The filter can be made of a shape memory alloy, which when in a delivery and/or retrieval orientation has at least a first portion that is in a narrowed configuration, and when deployed and set having an expanded configuration. The filtering portion, which is substantially conical, can be configured to be similarly narrowed during delivery and/or retrieval, and expanded after being deployed and set. This provides the free recovery shape. However, the conical portion can be configured to maintain substantially a constant size during deployment and after being deployed and set. The largest diameter portion of the filter has a diameter of sufficient size to contact the inner walls of the vessel. As such, the largest diameter portion of the filter can provide a force against the inner wall of the vessel so as to hold the filter at the site of deployment. The large diameter portion of the filter also has a wall contact disposed on the external surface. The wall contact is dimensioned sufficiently so as to separate the filter body from the inner surface of the body lumen. Accordingly, increasing the area of the wall contact can increase the contact area with the vessel and decrease the chance for the filter to move from the site of deployment. The force of the large diameter portion and wall contact applied to the inner surface of the vessel act together to anchor and stabilize the filter at the site of deployment within the vessel. The narrowed section, which includes the conical portion, is formed by strut elements or braids (e.g., filter elements) that provide a conduit having a progressively decreasing diameter from the large end to the small end of each funnel. The strut elements or braids can be provided in a spaced apart arrangement of an appropriate distance to capture particulates within the blood flow without substantially interfering with the normal blood flow.

Generally, a filter of the present invention can include at least a first set of interconnected strut elements (e.g., filter elements) that cooperatively define the body of the filter. Usually, each strut element can be defined by a cross-sectional profile as having a width and a thickness, and including a first end and a second end bounding a length. The stent element can be substantially linear, arced, rounded, squared, combinations thereof, or other configurations. The strut element can include a bumper, crossbar, connector, inter-connector, intersection, elbow, foot, ankle, toe, heel, medial segment, lateral segment, combinations thereof, or the like which are well known in the endoprosthetic arts. Generally, the strut element can be configured to a corresponding element of a stent.

The wall contacts can be formed into various shapes and sizes, and a range in the number of wall contacts can be varied for different uses. Generally, the wall contact is polymeric and dimensioned sufficiently to separate the filter body from the vessel wall and/or anchor the filter in place.

The present invention provides a filter having a free recovery shape that allows for easy delivery and retrieval. Accordingly, the figures illustrate embodiments of filters that have the free recovery shapes. While the filters are shown to have symmetrical portions that are substantially hourglass in shape, the filters can be substantially half of an hourglass, conical, or funnel-like in shape. As such, the embodiments of the filters of the present invention can be half of the shape that is shown in the figures.

FIG. 1A is a schematic representation of a filter 10 having a central axis 76, which is shown in side a view, in accordance with the present invention. The filter 10 has an hourglass-like shape that is defined by the filter body 12, which includes a first body portion 20, second body portion 32, first funnel body 44, second funnel body 56, and median body 68. The filter 10 is arranged such that the first body portion 20 is coupled to the first funnel body 44, which is coupled to the median body 68 which is coupled to the second funnel body 56 which is coupled to the second body portion 32. The filter body 12 can include a plurality of structural elements 14 that cooperate to provide structural integrity to the filter 10. The body 12 and body elements 14 can be shaped and/or otherwise configured similarly to an endoprosthesis configured for deployment into a body lumen, examples of which include lumen filters, stents, and the like. The structural elements 14 can include annular elements, helical elements, crossbars, connectors, junctions, braids, and other like features that are commonly employed in stent and/or filter endoprostheses.

The hourglass shape of the body 12 at least partially defines a first end 16 that includes a first opening 18 formed therein. The first end 16 is disposed at a longitudinal end of the body 12, and the first opening 18 can be substantially the same dimensions as the first end 16. The segment of the body 12 that defines the first end 16 is the first body portion 20. The first body portion 20 can have various shapes and sizes; however, it is depicted as being substantially cylindrical in FIG. 1A. The first body portion 20 defines a first large conduit 22 that is fluidly coupled with the first opening 18 such that an object can pass through the first opening 18 and into the first large conduit 22, or vice versa. The first large conduit 22 has a first large diameter 24 that has a uniform or varying dimension. The first large diameter 24 can be substantially uniform such that the first body portion 20 has a substantially uniform cross-sectional profile. The first body portion 20 and/or the first large conduit 22 has a first length 26 that extends from the first end 16 and/or first opening 18 to the opposite end of the first body portion 20 and/or first large conduit 22.

Additionally, the opposite end of the hourglass shape of the body 12 from the first end 16 at least partially defines a second end 28 that includes a second opening 30 formed therein. The second end 28 is disposed at a longitudinal end of the body 12, and the second opening 30 can be substantially the same dimensions as the second end 28. The segment of the body 12 that defines the second end 28 is the second body portion 32. The second body portion 32 can have various shapes and sizes; however, it is depicted as being substantially cylindrical in FIG. 1A, which is similar to the first body portion 20. The second body portion 32 defines a second large conduit 34 that is fluidly coupled with the second opening 30 such that an object can pass through the second opening 30 and into the second large conduit 34, or vice versa. The second large conduit 34 has a second large diameter 36 that has a uniform or varying dimension. The second large diameter 36 can be substantially uniform such that the second body portion 32 has a substantially uniform cross-sectional profile. The second body portion 32 and/or the second large conduit 34 has a second length 38 that extends from the second end 28 and/or second opening 30 to the opposite end of the second body portion 32 and/or second large conduit 34.

The first body portion 20 is fluidly coupled with a first funnel body 44 such that the end of the first body portion 20 opposite of the first end 16 and/or first opening 18 is coupled to the first funnel large end 40. As such, the first funnel large end 40 can be considered to be a junction with the first body portion 20. The first funnel body 44 also has a first funnel small end 42 that is opposite of the first funnel large end 40. As shown, the first funnel large end 40 has a larger diameter and/or opening compared to the first funnel small end 42. The first funnel body 44 defines a first funnel conduit 50 which is disposed therein. The first funnel body 44 and/or first funnel conduit 50 includes a first funnel diameter 46 that decreases from the first funnel large end 40 to the first funnel small end 42 such that the cross-sectional profile of the first funnel body 44 and/or first funnel conduit 50 correspondingly decreases. The first funnel body 44 and/or the first funnel conduit 50 has a first funnel length 48 that extends from the first funnel large end 40 to the opposite first funnel small end 42.

The second body portion 32 is fluidly coupled with a second funnel body 56 such that the end of the second body portion 32 opposite of the second end 28 and/or second opening 30 is coupled to the second funnel large end 52. As such, the second funnel large end 52 can be considered to be a junction with the second body portion 32. The second funnel body 56 also has a second funnel small end 54 that is opposite of the second funnel large end 52. As shown, the second funnel large end 52 has a larger diameter and/or opening compared to the second funnel small end 54. The second funnel body 56 defines a second funnel conduit 62 which is disposed therein. The second funnel body 56 and/or second funnel conduit 62 includes a second funnel diameter 58 that decreases from the second funnel large end 52 to the second funnel small end 54 such that the cross-sectional profile of the second funnel body 56 and/or second funnel conduit 62 correspondingly decreases. The second funnel body 56 and/or the second funnel conduit 62 has a second funnel length 60 that extends from the second funnel large end 52 to the opposite second funnel small end 54.

The first funnel small end 42 of the first funnel body 44 is coupled to the first median end 64 of the median body 68, and the second funnel small end 54 of the second funnel body 56 is coupled to the second median end 66 of the median body 68. This configuration disposes the median body 68 between the first funnel body 44 and the second funnel body 56. The median body 68 defines a median conduit 74, having a median diameter 70 and a median length 72. The median diameter 70 can have a dimension that is substantially the same from the first median end 64 to the second median end 66, or the dimension can be varied, such as increasing, decreasing, parabolic, and the like.

The filter 10 can be configured such that each corresponding portion along the central axis 76 is similar or different. For example, the first body portion 20 can have shapes and/or dimensions that are the same or different from the shapes and/or dimensions of the second body portion 32; the first funnel body 44 can have shapes and/or dimensions that are the same or different from the shapes and/or dimensions of the second funnel body 56. Also, the median body 68 can be configured such that the median conduit 74 is extremely small so that blood clot particulates do not pass therethrough. This allows the filter 10 to filter the blood. Also, the first length 26 of the first body portion 20 and/or the second length 38 of the second body portion 32 can be dimensioned to improve the static disposition of the filter 10 within a body lumen such that the filter 10 is substantially immobile after deployment. This can impart an enlarged contact surface with the body lumen that allows the filter 10 to have increased contact with the body lumen. Additionally, the first funnel length 48 and/or second funnel length 60 can be dimensioned to improve the filtering capability of the filter 10, wherein such dimension changes can include sharper or more gradual slopes of the conical shape. Moreover, the dimensions of the median body 68 can be modulated so as to change the filtering characteristics of the filter 10, where a smaller median conduit 74 can catch smaller particles and a larger median conduit 74 can allow larger particles to pass therethrough. Thus, the diameter, shape, and/or length of the median conduit 74 can be tailored for a particular body lumen and/or for the size of particulates to be captured and filtered from the body fluid.

Additionally, FIG. 1A illustrates the filter 10 having wall contacts 78a,b and 82a,b. The first wall contacts 78a,b are disposed on the filter body 12 on an exterior surface of the first body portion 20. As shown, the first body portion 20 includes a first wall contact 78a that is coupled to the filter body 12 by having fasteners 80a,b that are coupled to at least one of the structural elements 14. This can include the fasteners 80a,b extending through a hole (not shown) in a structural element 14 and coupling to the first wall contact 78a. The fasteners 80a,b can be any type of fastener element that can attach the first wall contact 78a with the first body portion 20 of the filter body 12. Additionally, a first opposite wall contact 78b is disposed on the external surface of the first body portion 20 of the filter body 12 opposite from the first wall contact 78a. The first opposite wall contact 78b is coupled to the first body portion of the filter body 12 by fasteners 80c,d, which can be substantially similar to fasteners 80a,b.

For example, the large diameters 24, 36 can be from about 0.001 mm to about 10 mm, from about 0.01 mm to about 5 mm, and/or about 0.1 mm to about 1 mm. The lengths 26, 38 can be from about 0 mm to about 50 mm, from about 0.001 to about mm, and/or about 0.1 mm to about 10 mm. The funnel diameters 46, 58 can be from about 0 mm to about 10 mm, from about 0.001 mm to about 5 mm, and/or about 0.01 mm to about 1 mm. The funnel lengths 48, 60 can be from about 0.01 mm to about 50 mm, from about 0.1 mm to about 25 mm, and/or about 0.5 mm to about 1 mm. The median diameter 70 can be from about 0 mm to about 1 mm, from about 0.0001 mm to about 0.5 mm, and/or about 0.001 mm to about 0.01 mm. The median length 72 can be from about 0 mm to about 50 mm, from about 0.001 mm to about 25 mm, and/or about 0.01 mm to about 10 mm. However, other sizes can be employed and determined by routine studies of the vasculature or other body lumen in which the filter 10 will be placed.

The second wall contacts 82a, b are disposed on the filter body 12 on an exterior surface of the second body portion 32. As shown, the second body portion 32 includes a second wall contact 82a that is coupled to the filter body 12 by having fastener 84a coupled to at least one of the structural elements 14. This can include the fastener 84a extending through a hole (not shown) in a structural element 14 and coupling to the second wall contact 82a. The fastener 84a can be any type of fastener element that can attach the second wall contact 82a with the second body portion 32 of the filter body 12. Additionally, a second opposite wall contact 82b is disposed on the external surface of the second body portion 32 of the filter body 12 opposite from the second wall contact 82a. The second opposite wall contact 82b is coupled to the second body portion 32 of the filter body 12 by fastener 84b, which can be substantially similar to fastener 84a.

The wall contacts 78, 82 are shown to have a length that is substantially similar to the body portion to which they are coupled. For example, first wall contacts 78a,b are shown to be substantially the same length as the first body portion 20, and the second wall contacts 82a,b are shown to be substantially the same length as the second body portion 32. However, any of the contacts can be any length with respect to the body portion to which they are coupled, which can be longer or shorter. Also, while one wall contact is shown to be disposed on a body portion in a given length, a plurality of wall contacts can be disposed on the body portion in a given length. For example, the first wall contact 78a can include a plurality of wall contacts that can be adjacently touching or separated along the first length 26 of the first body portion 20. Also, each of the first wall contacts 78a,b are shown to be coupled to the first body portion 20 via two fasteners 80 and each of the second wall contacts 82a,b are shown to be coupled to the second body portion 32 via one fastener 82; however, any number of fasteners can be used to couple a wall contact to the filter 10.

FIG. 1B is a schematic representation of a cross-sectional profile of the filter 10 taken at line 1B show in FIG. 1A, which mainly depicts the cross-sectional profile of the first body portion 20, the first funnel body 44, and the median conduit 74. As shown, and with further reference to FIG. 1A, the first body portion 20 has a diameter 24 that is substantially similar to the size of the first funnel large end 40. The first funnel body 44 narrows the first funnel conduit 50 until reaching the small opening of the median conduit 74, which has a small median diameter 70. The first funnel body 44 can include a plurality of structural elements 14 that cooperate to form filter apertures 15 that are filter pores. The size and/or shapes of the filter apertures 15 can be configured to be larger or smaller depending on the size of particulates to be trapped and filtered from the body fluid. For example the apertures 15 can have a dimension ranging from about 0.00001 mm to about 0.1 mm, from about 0.0001 mm to about 0.01 mm, and/or from about 0.001 mm to about 0.001 mm.

FIG. 1B also shows the first wall contact 78a to be disposed oppositely of the first opposite wall contact 78b. Additionally, the first body portion 20 can include additional first wall contacts 78c,d disposed around the outer surface of the body 12. While four wall contacts 78a-d are shown to be disposed on the outer surface of the first body portion 20, any number of wall contacts 78a-d can be used. Also, the wall contacts 78a-d can be systematically, evenly, randomly, or unevenly distributed around the circumference of the first body portion 20.

FIGS. 1A-1B also show an example of an embodiment of the configuration of the structural elements 14 and the corresponding filter apertures 15. As shown, the filter apertures 15 proximate to the first funnel large end 40 have substantially the same dimensions as the filter apertures 15 that are proximate to the first funnel small end 42. However, the filter apertures 15 proximate to the first funnel large end 40 can be larger than the filter apertures 15 that are proximate to the first funnel small end 42, or vice versa. However, the filter apertures 15 can have any functional shape and/or size to function as a filter pore.

FIGS. 2A-2D illustrate schematic representations of additional embodiments of an endoprosthesis in accordance with the present invention. As illustrated, the endoprosthesis can be configured into a filter for a body lumen.

FIG. 2A is a schematic representation of a side view of a filter 200 in accordance with the present invention. The filter 200 has a shape and size that is defined by a filter body 202 having an interconnected diamond pattern. As shown, the filter body 202 is in the shape of a double cone filter. That is, the filter body 202 is shaped substantially similarly to two cones 204, 206 that are coupled together at the median point 208. The various features of the filter body 202 can be configured similarly to the filter 100 of FIG. 1A. Accordingly, the first cone 204 can have an opening that allows a body fluid to flow therethrough with the filter body 202 forming a first cone 204 that decreases the cross-sectional profile until reaching the median point 208. The second cone 206 is substantially similar to the first cone 204; however, it is oriented in the opposite direction. This allows the filter 200 to be bi-directional and can be placed in the body lumen with either end receiving the flow of body fluid, and the opposite end being the exit for the body fluid.

FIG. 2A also shows first wall contacts 211a,b to be disposed on the first cone 204, and being coupled thereto via fasteners 212a,b. Also, second wall contacts 214a,b are shown to be disposed on and coupled to the second cone 206 via fasteners 216a,b. The wall contacts 211, 214 are shown to have an outer surface configured to conform to the wall of body lumen to provide a contact surface therewith, and to have an inner surface configured to conform to the sloped outer surface of the filter body 202.

Figure 2B:
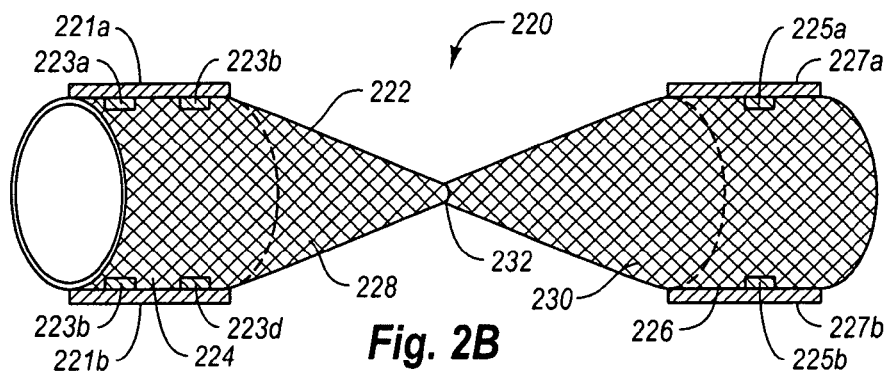

FIG. 2B is a schematic representation of a side view of another embodiment of a filter 220 in accordance with the present invention. The filter 220 has a shape and size that is defined by a filter body 222 having an interconnected square pattern. As shown, the filter body 222 is in the shape of an extended double funnel filter. That is, the filter body 222 is shaped substantially similarly to extended two funnels 228, 230 that have tubes 224, 226 coupled to the wide portion of the funnels 228, 230 that are in turn coupled together at the median point 232. The various features of the filter body 220 can be configured similarly to the filter 100 of FIG. 1A. Accordingly, the first funnel 228 can have an opening that allows a body fluid to flow therethrough with the filter body 222 having a first tube 224 that is coupled to a first funnel 228 that decreases the cross-sectional profile until reaching the median point 232. The second tube 226 and second funnel 230 are substantially similar to the first tube 224 and first funnel 228; however, it is oriented in the opposite direction. This allows the filter 220 to be bi-directional and can be placed in the body lumen with either end receiving the flow of body fluid, and the opposite end being the exit for the body fluid.

FIG. 2B also shows first wall contacts 221a,b to be disposed on the first tube 224, and being coupled thereto via fasteners 223a-d. Also, second wall contacts 227a,b are shown to be disposed on and coupled to the second tube 226 via fasteners 225a,b. The wall contacts 221, 227 are shown to have an outer surface configured to conform to the wall of body lumen to provide a contact surface therewith, and to have an inner surface configured to conform to the outer surface of the tubes 224, 226 of the filter body 222.

Figure 2C:
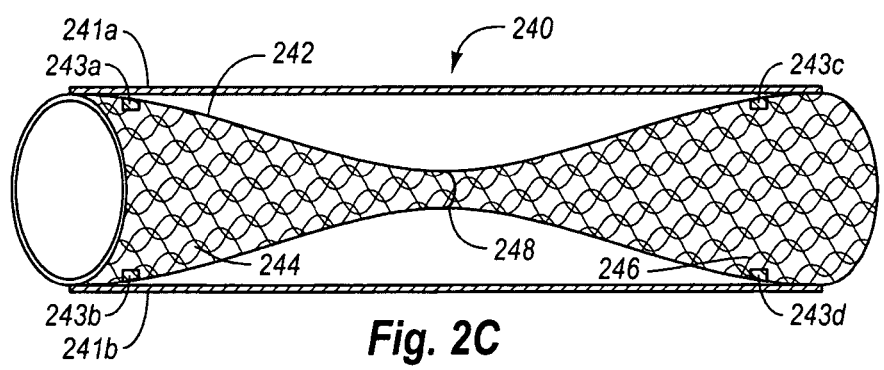

FIG. 2C is a schematic representation of a side view of another embodiment of a filter 240 in accordance with the present invention. The filter 240 has a shape and size that is defined by a filter body 242 having an interconnected sinusoidal pattern. As shown, the filter body 242 is in the shape of a double funnel filter with a conduit median 248 disposed between a first funnel 244 and a second funnel 246. That is, the filter body 242 is shaped substantially similarly to two funnels 244, 246 that are coupled together with a median conduit 248. The various features of the filter body 242 can be configured similarly to the filter 100 of FIG. 1A. Accordingly, the first funnel 244 can have an opening that allows a body fluid to flow therethrough with the filter body 242 forming a funnel that decreases the cross-sectional profile until reaching the median conduit 248, which can have any shape and size so as to filter selected particulate sizes from the body fluid. The second funnel 246 is substantially similar to the first funnel 244; however, it is oriented in the opposite direction on the other side of the median conduit 248. This allows the filter 240 to be bi-directional and can be placed in the body lumen with either end receiving the flow of body fluid, and the opposite end being the exit for the body fluid.

FIG. 2C also shows a first wall contact 241a to be disposed on a first side of the filter body 242, and a second wall contact 241b to be disposed on a second side of the filter body 242. The first and second wall contacts 241a,b are coupled to the filter body 242 via fasteners 243a-d. The wall contacts 241a,b are shown to have an outer surface configured to conform with the wall of a body lumen to provide a contact surface therewith, and to have an inner surface configured to conform with the shape of the outer surface of the filter body 242.

Figure 2D:
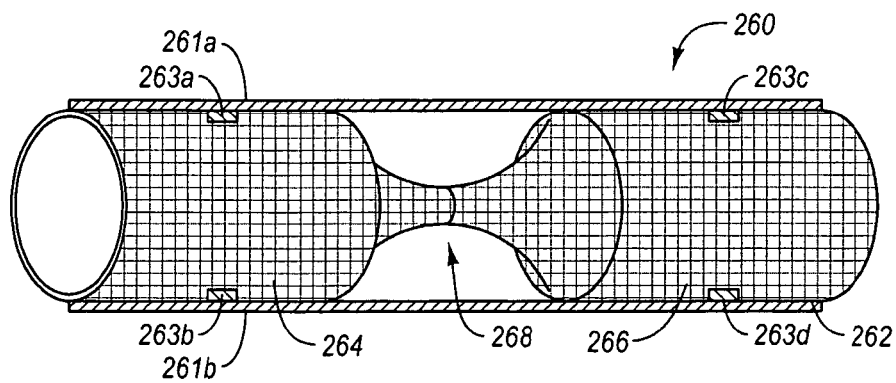

FIG. 2D is a schematic representation of a side view of another embodiment of a filter 260 in accordance with the present invention. The filter 260 has a shape and size that is defined by a filter body 262 having a checkerboard pattern. As shown, the filter body 262 is in the shape of a tube that has a parabolically narrowed central region. That is, the filter body 262 is shaped substantially similarly to two tubes 264, 266 that are coupled together at a parabolic median 268. The various features of the filter body 262 can be configured similarly to the filter 100 of FIG. 1A. Accordingly, the first tube 264 can have an opening that allows a body fluid to flow therethrough with the filter body 262 having a parabolic median 268 decreases the cross-sectional profile until reaching a central point, and then the parabolic median 268 increases in cross-sectional profile until reaching the second tube 266. The second tube 266 is substantially similar to the first tube 264; however, it is oriented in the opposite direction. This allows the filter 260 to be bi-directional and can be placed in the body lumen with either end receiving the flow of body fluid, and the opposite end being the exit for the body fluid.

FIG. 2D also shows wall contacts 261a,b to be disposed on the filter body 262, and being coupled thereto via fasteners 263a-d. The wall contacts 261a,b are shown to have an outer surface configured to conform with the wall of a body lumen to provide a contact surface therewith, and to have an inner surface configured to conform with the outer surface of the tubes 264, 266 of the filter body 262. As shown, the wall contacts 261a,b have a length commensurate with the length of the entire filter body 262. As such, the wall contacts 261a,b extend from the first portion 264 over the parabolic portion 268 and across the second portion 266.

FIGS. 3A-3D illustrate schematic representations of embodiments of the substantially cone-shaped filter portion of an endoprosthesis in accordance with the present invention. As illustrated, the cone-shaped filter portion can have different configurations in order to filter or selectively filter particulates from a body fluid in a body lumen.

FIG. 3A illustrates an embodiment of a substantially funnel-shaped filter 300 in accordance with the present invention. As shown, the funnel-shaped filter 300 has a twisted funnel-shaped body 301 that is shaped by structural elements 303 (i.e., filter elements) that cooperate to form the filter 300. The funnel-shaped filter 300 is illustrated to show the features of the filter 300 between the funnel large end 302 and the funnel small end 304. The structural elements 303 are formed by a plurality of radial members 306 that spiral from the funnel small end 304 to the funnel large end 302. As such, the radial members 306 cooperatively form apertures 310 that increase in cross section from the funnel small end 304 to the funnel large end 302. The smaller cross section at the funnel small end 304 allows for the filtering of smaller particles in the body fluid and the larger cross section at the funnel large end 302 allows for similarly sized particles to pass therethrough. The apertures 310 thereby trap larger particles near the funnel small end 304 and allow smaller particles to pass through near the funnel large end 302. Optionally, the funnel-shaped filter 300 can include circular members 308 as shown by the dashed lines. The circular members 308 can cooperate with the radial members 306 so as to form much smaller apertures 310 that are configured similarly to pores of standard filters. This allows for size-exclusion selection of which particles will be filtered from the body fluid and which particles will be allowed to pass through the filter 300 and continue flowing in the body lumen.

Additionally, FIG. 3A shows four wall contacts 305a-d being evenly disposed about the circumference of the filter body 301. Each of the wall contacts 305a-d are coupled to the filter body 301 via fasteners 307a-d. The outer surface of each of the wall contacts 305a-d is curved so as to conform to the inner surface of a body lumen, and the inner surface of each of the wall contacts 305a-d is curved so as to conform to the outer surface of the filter body 301.

FIG. 3B illustrates an embodiment of a substantially funnel-shaped filter 320 in accordance with the present invention. As shown, the funnel-shaped filter 320 has a target-shaped body 321 that is shaped by structural elements 323 that cooperate to form the filter 320. The funnel-shaped filter 320 is illustrated to show the features of the filter 320 between the funnel large end 322 and the funnel small end 324. The structural elements 323 are formed by a plurality of radial members 326 that extend substantially linearly or straight without spiraling from the funnel small end 324 to the funnel large end 322. As such, the radial members 326 cooperatively form apertures 340 that increase in cross section from the funnel small end 324 to the funnel large end 322. The smaller cross section at the funnel small end 324 allows for the filtering of smaller particles in the body fluid and the larger cross section at the funnel large end 322 allows for similarly sized particles to pass therethrough. The apertures 340 thereby trap larger particles near the funnel small end 324 and allow smaller particles to pass through near the funnel large end 322. As shown, the funnel-shaped filter 320 includes circular members 328. The circular members 328 cooperate with the radial members 326 so as to form much smaller apertures 340 that are configured similarly to pores of standard filters. This allows for size-exclusion selection of which particles will be filtered from the body fluid and which particles will be allowed to pass through the filter 300 and continue flowing in the body lumen.

Additionally, FIG. 3B shows two wall contacts 325a,b being disposed on the outer surface of the filter body 321 opposite from each other. Each of the wall contacts 325a,b are coupled to the filter body 321 via fasteners 327a,b. The outer surface of each of the wall contacts 325a,b is flat so as to apply differential pressure to the inner surface of a body lumen, which allows the wall contacts 325a,b to degrade and then conform to the inner surface of the body lumen. The inner surface of each of the wall contacts 325a,b is curved so as to conform to the outer surface of the filter body 321.

FIG. 3C illustrates an embodiment of a substantially funnel-shape filter 350 in accordance with the present invention. As shown, the funnel-shaped filter 350 has a checkerboard-shaped body 351 that is shaped by structural elements 353 that cooperate to form the filter 350. The funnel-shaped filter 350 is illustrated to show the features of the filter 350 between the funnel large end 352 and the funnel small end 354. The structural elements 353 are formed by a plurality of vertical members 356 and a plurality of horizontal members 358 that cooperatively form apertures 360 that are substantially the same size from the funnel small end 354 to the funnel large end 352. The substantially similar apertures 360 at the funnel small end 354 and funnel large end 352 allows for the filtering of the same sized particles in the body fluid so that there is a size exclusion cutoff size. Accordingly, same sized apertures 360 thereby trap the same size particles near the funnel small end 354 and the funnel large end 352. This allows for size-exclusion selection of which particles will be filtered from the body fluid and which particles will be allowed to pass through the filter 350 and continue flowing in the body lumen.

Additionally, FIG. 3C shows two wall contacts 355a,b being disposed on the outer surface of the filter body 351 opposite from each other. Each of the wall contacts 355a,b are coupled to the filter body 351 via fasteners 357a,b. The outer surface of each of the wall contacts 355a,b is flat, and inner surface of each of the wall contacts 355a,b is also flat. The wall contacts 355a,b are made from a malleable and/or flexible material that allows the wall contacts 355a,b to bend so as to conform with the inner surface of the body lumen and the outer surface of the filter body 351.

FIG. 3D illustrates an embodiment of a substantially funnel-shape filter 370 in accordance with the present invention. As shown, the funnel-shaped filter 370 has a wheel spoke-shaped body 371 that is shaped by structural elements 373 that cooperate to form the filter 370. The funnel-shaped filter 370 is illustrated to show the features of the filter 370 between the funnel large end 372 and the funnel small end 374. The structural elements 373 are formed by a plurality of radial members 376 that extend substantially linearly or straight without spiraling from the funnel small end 374 to the funnel large end 372. As such, the radial members 376 cooperatively form apertures 378 that increase in cross section from the funnel small end 374 to the funnel large end 372. The smaller cross section at the funnel small end 374 allows for the filtering of smaller particles in the body fluid and the larger cross section at the funnel large end 372 allows for similarly sized particles to pass therethrough. The apertures 378 thereby trap larger particles near the funnel small end 374 and allow smaller particles to pass through near the funnel large end 372. This allows for size-exclusion selection of which particles will be filtered from the body fluid and which particles will be allowed to pass through the filter 370 and continue flowing in the body lumen.

Additionally, FIG. 3D shows two wall contacts 375a,b being disposed on the outer surface of the filter body 371 opposite and from each other because they cooperate to form an outer tubular shape that extends around the circumference of the filter body 371. Each of the wall contacts 375a,b are coupled to the filter body 371 via fasteners 377a,b. The body of each wall contact 375a,b is configured as a half tube so that the combined outer surface of the wall contacts 375a,b forms a tube that conforms to the shape of the inner surface of a body lumen. The inner surface of each of the wall contacts 375a,b is also a half tube so that the combined inner surface area of the wall contacts 375a,b circumnavigates around the entire outer surface of the filter body 371.

FIG. 3E illustrates an embodiment of a filter 380 in accordance with the present invention. As shown, the filter 380 has a sectioned spiral-shaped body 381 that is shaped by structural elements 383 that cooperate to form the filter 380. The cone-shaped filter 380 is illustrated to show the features of the filter 380 between the funnel large end 382 and the funnel small end 384. The structural elements 383 are formed by a single spiral member 386 that spirals from the funnel small end 384 to the funnel large end 382. As such, the spiral member 386 cooperatively forms an aperture 390 that spirally extends and optionally increases in cross section from the funnel small end 384 to the funnel large end 382. Optionally, the filter 380 can include radial members 388 as shown by the dashed lines, wherein the radial members 388 can be substantially similar to other radial members depicted in the other embodiments. The radial members 388 can cooperate with the spiral member 386 so as to form much smaller apertures 390 that are configured similarly to pores of standard filters. This allows for size-exclusion selection of which particles will be filtered from the body fluid and which particles will be allowed to pass through the filter 380 and continue flowing in the body lumen.

Additionally, FIG. 3E shows a wall contact 385 that is disposed on the outer surface of the filter body 381 to form an outer tubular shape that extends around the circumference of the filter body 381. The wall contact 385 is coupled to the filter body 381 via fasteners (not shown), affixation, coating, or other means of attaching concentric tubes. The body of the wall contact 385 is configured as a tubular shape so that the outer surface of the wall contact 385 forms a tube that conforms to the shape of the inner surface of a body lumen. The inner surface of the wall contact 385 is also a tubular shape so that the combined inner surface area of the wall contact 385 circumnavigates around the entire outer surface of the filter body 381.

FIG. 3F illustrates an embodiment of a filter 392 in accordance with the present invention. As shown, the filter 392 has a sectioned spiral-shaped body 391 that is shaped by structural elements 393 that cooperate to form the filter 392. The cone-shaped filter 392 is illustrated to show the features of the filter 392 between the funnel large end 394 and the funnel small end 396. The structural elements 393 are formed by a single spiral member 398 that spirals from the funnel small end 396 to the funnel large end 394. As such, the spiral member 398 cooperatively forms an aperture 399 that spirally extends and increases in cross section from the funnel small end 396 to the funnel large end 394. This is because the spiral member 398 is wound tighter at the funnel small end 396 compared to the funnel large end 394. However, the spiral member 398 can be wound tighter at the funnel large end 394 compared to the funnel small end 396, or any other variation. This allows for size-exclusion selection of which particles will be filtered from the body fluid and which particles will be allowed to pass through the filter 392 and continue flowing in the body lumen.

Figure 4A:
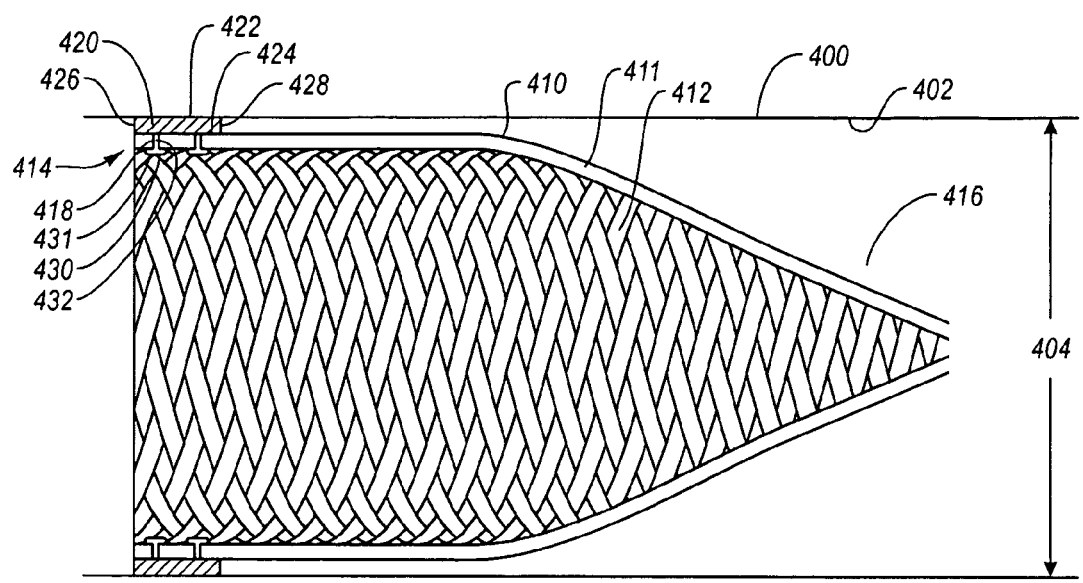
FIG. 4A is a schematic representation illustrating a side view of an embodiment of a conical filter having wall contacts coupled to the filter via a fastener inserted through fastener holes.
Figure 4B:
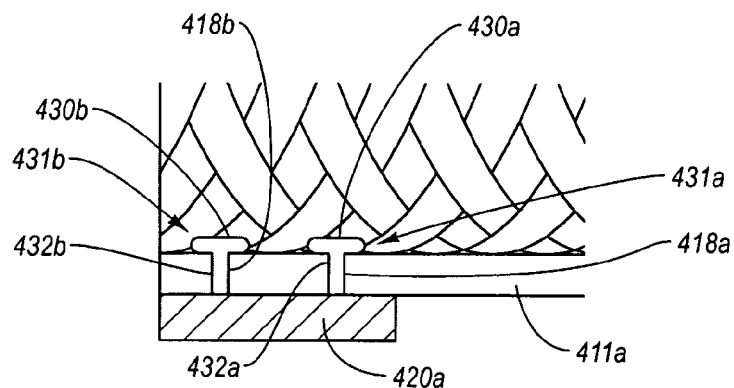
FIG. 4B is a magnified cutaway side view of FIG. 4A illustrating an embodiment of the fastener inserted through fastener holes in order to couple the wall contact to the filter.
Figure 4C:
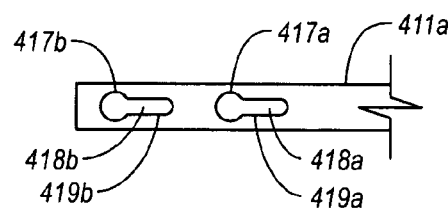
FIG. 4C is a magnified cutaway view of FIG. 4B illustrating an embodiment of the fastener holes having a keyway slot shape.

FIGS. 4A-4C are schematic representations of a filter 410 disposed within a body lumen 400. The body lumen 400 includes an inner surface 402 that receives the filter 410. As such, the body lumen 400 has a diameter 404 that is similar in size to the filter 410. The filter 410 can be substantially similar to any of the filters depicted and/or described in connection with the present invention.

As shown, the filter 410 is defined by a filter body 411 that has a first end 414 and an opposite second end 416. The first end 414 is configured for receiving a flow of body fluid within the body lumen 400, and the second end 416 is configured for filtering particulates from the body fluid and to allow the body fluid to exit the filter 410. The filter body 411 includes a fastener hole 418 that can receive a fastener 431 that couples the wall contact 420 with the filter body 411.

The wall contact 420 includes an outer surface 422 that is configured to contact the inner surface 402 of the body lumen 400. Additionally, the wall contact 420 includes an inner surface 424 that is configured to contact the filter body 411. The wall contact 420 also has a first end 426 and an opposite second end 428. The inner surface 424 of the wall contact 420 is configured to receive the fastener 431, wherein the fastener 431 can be permanently or removably coupled thereto.

The fastener 431 includes a shaft 432 and a head 430. The shaft 432 is configured to be inserted through and fit within the fastener hole 418. The head 430 is configured to have a larger size than at least a portion of the fastener hole 418 so that the head 430 can be positioned not to slide into the fastener hole 418, which functions to hold the fastener 431 in position and couple the wall contact 420 with the filter body 411.

FIG. 4B shows a first fastener 431a and a second fastener 431b coupling a wall contact 420a to the filter body 411a. The filter body 411a includes a first fastener hole 418a that receives the first shaft 432a so that the first head 430a holds the wall contact 420a to the filter body 411a. Additionally, the filter body 411a includes a second fastener hole 418b that receives the second shaft 432b of the second fastener 431b so that the second head 430b holds the wall contact 420a to the filter body 411a. In the instance the fasteners 431a,b are permanently affixed to the wall contact 420a, a portion of the fastener holes 418a,b are at least as large as the fastener heads 430a,b so that they can fit therethrough during the process of coupling the wall contact 420a with the filter body 411a.

FIG. 4C is a schematic representation of one embodiment of a filter body 411a that is configured to removably receive a wall contact 420a. As such, the filter body 411a includes the fastener holes 418a,b being formed into the shape of a keyway slot. The keyway slot shape of the fastener holes 418a,b has a large opening portion 417a,b that is large enough to receive the fastener head 430a,b therethrough. Additionally, the keyway slot shape of the fastener holes 418a,b has a small opening portion 419a,b that is small enough to inhibit the fastener head 430a,b from moving into the faster hole 418a,b, but is large enough to receive the fastener shaft 432a,b therein. The keyway slot shape configuration thereby allows the fastener 431a,b to be inserted through the large opening portion 417a,b and then allows the fastener shaft 432a,b to be slipped or otherwise passed into the small opening portion 419a,b so that the fastener head 430a,b is disposed on the inner surface of the filter body 411a so as to securely hold the wall contact 420a against the external surface of the filter body 411a.

The size of the aperture or apertures, which function as pores, can be dimensioned as needed for different applications. As such, the aperture or apertures can have smaller dimensions when the filter is designed to filter out smaller particulates. Conversely, the aperture or apertures can have larger dimensions when smaller particulates are needed to be filtered, but the apertures or apertures still filter out particles larger than the cutoff dimension. For example the apertures can have a dimension ranging from about 0.00001 mm to about 0.1 mm, from about 0.0001 mm to about 0.01 mm, and/or from about 0.001 mm to about 0.001 mm.

The size, shape, and number of the wall contacts for a given filter can be modulated as needed for different applications. The wall contacts can have smaller dimensions when used in smaller vessels. Conversely, the wall contacts can have larger dimensions when used in larger vessels For example, the wall contacts can have a thickness that can range from about 0.00001 mm to about 1 mm, from about 0.0001 mm to about 0.1 mm, and/or from about 0.001 mm to about 0.01 mm. The wall contacts can have a width that can range from 0.00001 mm to about 1 mm, from about 0.0001 mm to about 0.1 mm, and/or from about 0.001 mm to about 0.01 mm. The wall contacts can have a longitudinal length that can range from about 0 mm to about 50 mm, from about 0.001 to about 25 mm, and/or about 0.1 mm to about 10 mm.

The fasteners of the present invention can be configured as any standard fastener used in the medical arts to attach one medical component to another medical component. Such fasteners can be in the form of an adhesive, screw, nail, cotter pin, bolts, nuts, and the like. The fastener can be the same or similar material as the filter and/or the wall contact or a different material. The fastener can be integrated, permanently coupleable, or removably coupleable with the wall contact. For example, the fastener system can include the wall contact having a bolt-like protrusion extending through the fastener hold of the filter with a nut securing the wall contact to the filter by being fitted onto the bolt-like protrusion. In another example, the fastener is substantially a nail-like structure integrated with the wall contact or formed therewith. In yet another example, the fastener is a screw that fits through the fastener hole and into the wall contact, where the screw head is larger than at least a portion of the fastener hole. In still yet another example, the wall contact includes a recess, such as a threaded recess, to receive the fastener.

Additionally, a filter can have at least one wall contact. For example, the filter can have one wall contact that extends around the entire circumference of the external surface of the filter. The filter can have two wall contacts that are disposed oppositely from each other. The filter can have 3, 4, 5, or more wall contacts that are distributed around the circumference of the external surface of filter. The filter can have wall contacts that are adjacent and/or touching so as to extend partially through fully around the entire circumference of the external surface of the filter.

The filter can be inserted into the vessel through a catheter or other similar type device in a compressed or flattened form, where the filter expands in the vessel, such that the wall contacts disposed on the external surface of the filter contact the vessel so as to stabilize and secure the position of the filter within the vessel. Such a compressed or flattened delivery configuration can be achieved by pulling apart, increasing the axial distance between, the filter ends. This longitudinally stretches and radially compresses the filter. In this manner, the maximum diameter sections of each of the larger ends are drawn radially toward the central longitudinal axis. Upon deployment and setting, the material properties of the filter expand, drawing together, decreasing the axial distance between, the filter ends. This longitudinally compresses and radially expands the filter. In this manner, the maximum diameter end sections of the filter are radially expanded toward the vessel wall such that the wall contacts are positioned against the vessel wall. It is contemplated that the filter can be inserted either through a femoral or jugular approach as previously described. However, the filter can be configured for placement in almost any vessel or other body lumen.

To adequately hold the filter in place, the wall contacts can be disposed on the larger diameter ends of the filter so as to exert a radial force normal to the vena cava walls. The strut elements, and thereby the larger diameter ends, are sufficiently resilient to be compressed into the introducer catheter and to regain their original shape after being released.

III. Deploying Filter

The filters of the present invention are configured for use in a body lumen so as to filter the body fluid that flows through the body lumen. This can filter particulates that are larger than a selected size from the body fluid. As such, the present invention includes a method of delivering a lumen filter into a body lumen of a subject. Such a method includes: providing a lumen filter as described herein; orienting the filter into a delivery orientation by longitudinally elongating the filter body such that the larger ends filter have a reduced dimension with a cross section that is smaller than the body lumen; inserting the filter in the delivery orientation into a delivery device, such as a deliver catheter that can be configured substantially as a catheter for delivering a stent; delivering the elongated filter body to a desired deployment site within the body lumen of the subject; removing the filter from the delivery device; and longitudinally shortening the filter body such that the larger ends of the filter each have an enlarged dimension that applies radial forces to an inner wall of the body lumen.

FIG. 5A is a schematic representation illustrating a delivery system 500 for delivering a filter 520a into a body lumen 540, such as a blood vessel like the vena cava. The delivery system 500 includes an endoprosthesis delivery catheter 502 configured for delivering a filter 520a that is retained by the delivery catheter 502 in a delivery orientation (e.g., longitudinally elongated and/or radially compressed). The delivery catheter 502 includes a delivery member 504 that defines a delivery lumen 507 that is shaped and dimensioned to retain the filter 520a in the delivery orientation. Accordingly, the delivery member 504 is substantially tubular and configured similarly as any delivery catheter member. An internal surface 506 defined by the delivery member 504 holds the filter 520a within the delivery catheter 502.

The filter 520a is substantially as shown in FIG. 5A, and includes a body 522 having a first large portion 524 coupled to a first funnel 528 that is coupled to a second funnel 530 through an intermediate portion 532, wherein the second funnel 530 is coupled to a second large portion 526 so as to form the free recovery form. The first wall contacts 521a,b are disposed on the first large portion 524, and are coupled thereto via fasteners 523a-d. Also, second wall contacts 527a,b are shown to be disposed on and coupled to the second large portion 526 via fasteners 525a,b.

The delivery system 500 delivers the filter 520a with a delivery catheter 502 similarly to the method of delivering other endoprostheses into a body lumen. As such, an insertion site (not shown) is formed through the skin (not shown) that traverses into a body lumen 540. A guidewire (not shown) is then inserted through the insertion site, through the body lumen 540, to the delivery site 544. A catheter (not shown) is then inserted into the body lumen 540 to the delivery site 544 over the guidewire, and the guidewire is optionally extracted. The delivery catheter 502 is then inserted through the catheter (not shown) until reaching the delivery site 544 and the catheter (not shown) is withdrawn.

Optionally, the catheter is the delivery catheter 502, and in this instance, the delivery catheter 502 is retained at the delivery site 544 and the filter 520a is delivered to the delivery site 544 through the lumen 507 of the delivery catheter 502. A pusher 510 can be used to push the filter 520a within the lumen 507 of the delivery catheter 502 to the delivery site 544.

Accordingly, the delivery system 500 is inserted through percutaneous insertion site (not shown) that traverses from the skin (not shown) into the body lumen 540 until reaching the delivery site 544. The pusher 510 includes a distal end 512 that pushes the filter 520a from the distal end 508 of the delivery member 504. This is shown by the arrow pointing toward the distal end 508 of the delivery member 504, which shows the relative movement of the pusher 510 and thereby the filter 520a relative to the delivery member 504 and body lumen 540. Alternatively, the filter 520a can be disposed at the distal end 508 of the delivery member 504, and the pusher 510 holds the filter 520a at the delivery site 544 and the delivery member 504 is retracted over the filter 520a and pusher 510, which is shown by the arrows. Thus, the pusher 510 can push the filter from the delivery catheter 502 or the delivery member 504 can be withdrawn over the filter 520a and pusher 510 in order to deploy the filter 520a.

FIG. 5B illustrates a filter 520b in the deployed configuration at the delivery site 544 within the body lumen 540. As such, the filter 520 is longitudinally shortened and radially expanded so as to contact the inner wall 542 of the body lumen 540.

In one embodiment, the present invention can include a method of extracting a filter from the body lumen, which can include: inserting a filter-extracting medical device into the body lumen so as to come into contact with the filter; engaging the filter-extracting medical device with the filter; longitudinally elongating the filter body such that the larger ends of the filter have a reduced dimension with a cross section that is smaller than the body lumen; and retrieving the elongated filter body from the desired deployment site within the body lumen of the subject. Optionally, the elongated filter can be received into the filter-extracting medical device, which can be substantially similar to a catheter.

In one embodiment, at least one of delivering or retrieving the filter is performed with a catheter. Catheters configured for delivering and/or retrieving endoprostheses from a body lumen can be adapted for delivering and/or retrieving the filter of the present invention.

IV. Filter Members

In one embodiment, the filter may be formed from a plurality of strut members (i.e., filter members) that are interconnected together similar to the interconnected structure of annular element, such as a stent. The members can be formed of shape memory materials (SMM), where multiple types of SMMs can be employed together in a single filter.

In one embodiment, the strut member of the filter can be formed from several wires braided together in order to produce a braided wire with a desired outer diameter. Furthermore, a single wire may be encapsulated in a multi-strand braid. The braided wires can include a combination of SMMs, such that the combination of number braided wires and elements permits a desired filter function during deployment, filtering, and extraction.

In one embodiment, the body of the filter can be formed from a plurality of braided members. That is, the braided members can be substituted for the strut members, but be disposed in a braided configuration. For example, elongate members similar in form and function to the strut members can be substituted for the strut members and be fashioned together so as to form a braided body. Such elongate members themselves can be prepared from braided wires or other braided members that have much smaller diameters compared to the elongate members and/or strut members.

In one embodiment, the filter may be formed from a plurality of strut members that are interconnected together similar to the interconnected structure of an annular element, such as a stent. The members can be formed of shape memory materials (SMM), where multiple types of SMMs can be employed together in a single filter.

In one embodiment, each strut member can include a plurality of braided wires. The strut members can be substantially in the shape of a ribbon. That is, the strut member can have a substantially flat shape. The strut members can have a circular, oval, square, triangular, rectangular, polygonal, or other shape. In a method of manufacture, the braided wires forming the strut elements are heat set in the braid. The braided wires can be coated/jacketed with the biocompatible, biodegradable, and/or bioneutral material.

In presently described embodiments, strut elements having a rectangular, ribbon, or strip cross-sectional profile is employed, though oval-shaped or round cross-sections can also be employed. In the case of rectangular or oval cross-section, the strut element can be oriented so that the long dimension is parallel with and adjacent to the vena cava wall, with the narrow direction arranged radially. The thickness of the strut element is between 0.003 and 0.015 inch and/or between 0.005 and 0.009 inch. The width of the strut element is between 0.020 and 0.045 inch and/or between 0.025 and 0.035 inch.

In one embodiment, the large diameter portions of the filter can include an outer coating. The outer coating can be biocompatible, optionally biodegradable, and cover at least a portion of the large diameter portions that contact the body lumen. The coating can leave the apertures between the strut elements or braids open, or it can seal the apertures so as to provide a sleeve. As such, the outer coating can be configured to prevent adhesion of the tissue of the vessel to the filter. As such, the filter can be removed without substantially tearing or damaging the repaired vessel.

Furthermore, the filter, such as in the coating described above, can include a drug or pharmaceutical agent. The drug can include an anti-restenotic drug which decreases or prevents encapsulation of the filter with tissue growth. Exemplary anti-restenotic drugs include sirolimus, everolimus, taxol, paclitaxel, and the like. Additionally, a drug can be provided which promotes healing in the vessel adjacent to the filter.

The filters of the present invention can be made of a variety of materials, such as, but not limited to, those materials which are well known in the art of endoprosthesis manufacturing. This can include, but not limited to, a filter having a primary material for the large portions and the tapered portions. Alternatively, the tapered central portion can be made of a different material compared to the large end portions. Generally, the materials for the filter can be selected according to the structural performance and biological characteristics that are desired.

In one configuration, the large end portions and/or the tapered central portions include a primary material. The large end portions and/or the tapered central portions can include resiliently flexible materials or rigid and inflexible materials. For example, materials such as Ti3Al2.5V, Ti6Al4V, 3-2.5Ti, 6-4Ti and platinum may be particularly good choices for adhering to a flexible material, such as, but not limited to, Nitinol and providing good crack arresting properties. The use of resiliently flexible materials can provide shock-absorbing characteristics to the large end portions and/or the tapered central portions, which can also be beneficial for absorbing stress and strains, which may inhibit crack formation at high stress zones. For example, types of materials that are used to make an endoprosthesis can be selected so that the endoprosthesis is capable of being collapsed during placement and expanded when deployed. Usually, the endoprosthesis can be self-expanding, balloon-expandable, or can use some other well-known configuration for deployment.

In one embodiment, a filter of the present invention can include a material made from any of a variety of known suitable materials, such as a shape memory material (SMM). For example, the SMM can be shaped in a manner that allows for restriction to induce a substantially tubular, linear orientation while within a delivery shaft, but can automatically retain the memory shape of the filter once extended from the delivery shaft. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys (SMA) including metal alloys, or shape memory plastics (SMP) including polymers.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. This can include the specific sizes of the large end portions and/or the tapered central portions. The main types of SMAs are as follows: copper-zinc-aluminium; copper-aluminium-nickel; nickel-titanium (NiTi) alloys known as nitinol; and cobalt-chromium-nickel alloys or cobalt-chromium-nickel-molybdenum alloys known as elgiloy alloys. The temperatures at which the SMA changes its crystallographic structure are characteristic of the alloy, and can be tuned by varying the elemental ratios.

For example, the primary material of a filter can be of a NiTi alloy that forms superelastic nitinol. In the present case, nitinol materials can be trained to remember a certain shape, straightened in a shaft, catheter, or other tube, and then released from the catheter or tube to return to its trained shape. This also includes the hourglass shape or the shape of the large end portions and/or the tapered central portions. Also, additional materials can be added to the nitinol depending on the desired characteristic.

A Shape Memory Plastic (SMP) can be fashioned into a filter in accordance with the present invention. When an SMP encounters a temperature above the lowest melting point of the individual polymers, the blend makes a transition to a rubbery state. The elastic modulus can change more than two orders of magnitude across the transition temperature (Ttr). As such, an SMP can form into a desired shape of a filter, braid, and/or strut element by heating it above the Ttr, fixing the SMP into the new shape, and cooling the material below Ttr. The SMP can then be arranged into a temporary shape by force, and then resume the memory shape once the force has been applied. Examples of SMPs include, but are not limited to, biodegradable polymers, such as oligo($\epsilon$-caprolactone) diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

A filter having an SMM or suitable superelastic material and other suitable layers can be compressed or restrained in its delivery configuration (e.g., longitudinally elongated and radially compressed) within a delivery device using a sheath or similar restraint, and then deployed to its desired deployment configuration (e.g., longitudinally compressed and radially expanded) at a deployment site by removal of the restraint as is known in the art. A filter made of a thermally-sensitive material can be deployed by exposure of the filter to a sufficient temperature to facilitate expansion as is known in the art.

In one embodiment, the filter, braid, and/or strut element can include a variety of known suitable deformable alloy metal materials, including stainless steel, silver, platinum, tantalum, palladium, cobalt-chromium alloys or other known biocompatible alloy metal materials.

In one embodiment, the filter can include a suitable biocompatible polymer in addition to or in place of a suitable metal. The polymeric filter can include biodegradable or bioabsorbable materials, which can be either plastically deformable or capable of being set in the deployed configuration. If plastically deformable, the material can be selected to allow the filter to be expanded in a similar manner using an expandable member so as to have sufficient radial strength and scaffolding and also to minimize recoil once expanded. If the polymer is to be set in the deployment configuration, the expandable member can be provided with a heat source or infusion ports to provide the required catalyst to set or cure the polymer. Alternative known delivery devices and techniques for self-expanding endoprostheses likewise can be used. That is, the filter can be delivered and deployed much like other endoprostheses, such as stents.

Examples of such biocompatible materials for the filter can include a suitable hydrogel, hydrophilic polymer, biodegradable polymers, bioabsorbable polymers and bioneutral polymers. Examples of such polymers can include poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, or the like.

Furthermore, the filter can be formed from a ceramic material. In one aspect, the ceramic can be a biocompatible ceramic which optionally can be porous. Examples of suitable ceramic materials include hydroxylapatite, mullite, crystalline oxides, non-crystalline oxides, carbides, nitrides, silicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like. Optionally, the ceramic can be provided as sinterable particles that are sintered into the shape of a filter, braid, and/or stent element.

Moreover, the filter can include a radiopaque material to increase visibility during placement. Optionally, the radiopaque material can be a layer or coating any portion of the filter. The radiopaque materials can be platinum, tungsten, silver, stainless steel, gold, tantalum, bismuth, barium sulfate, or a similar material.

It is further contemplated that the external surface and/or internal surface of the filter, braid, and/or strut element (e.g., exterior and luminal surfaces) can be coated with another material having a composition different from the primary filter material. The use of a different material to coat the surfaces can be beneficial for imparting additional properties to the filter, such as providing radiopaque characteristics, drug-reservoirs, and improved biocompatibility.

In one configuration, different external surfaces of a filter, such as a low stress zone less susceptible to flexing, can be coated with functional layers of an imaging compound or radiopaque material. The radiopaque material can be applied as a layer at low stress zones of the filter. Also, the radiopaque material can be encapsulated within a biocompatible or biodegradable polymer and used as a coating. For example, the suitable radiopaque material can be palladium, platinum, tungsten, silver, stainless steel, gold, tantalum, bismuth, barium sulfate, or a similar material. The radiopaque material can be applied as layers on selected surfaces of the filter using any of a variety of well-known techniques, including cladding, bonding, adhesion, fusion, deposition or the like.

V. Wall Contacts

The wall contacts of the present invention can be provided in various sizes, shapes, and compositions for different applications. Generally, the wall contacts are sized appropriately for being deployed adjacent to a lumen filter for use in a body lumen of a subject. The wall contacts are shaped to be compatible with the filter and body lumen. The composition of the wall contacts can by substantially any polymeric material; however, biodegradable wall contacts can be advantageous.

In one embodiment, the wall contact further includes a shape such as the following: a square to rectangular block cross section; a square to rectangular block cross section having a long dimension that extends from the external surface of the filter body; a square to rectangular block cross section having a convex surface coupled to the external surface of the filter body; a square to rectangular block cross section having a concave surface coupled to the external surface of the filter body and an opposite convex surface configured to conform with the inner wall of the body lumen; an arc-shaped cross section having a concave surface coupled to the external surface of the filter body and an opposite convex surface configured to conform with the inner wall of the body lumen or an arc-shaped cross section having a concave surface coupled to the external surface of the filter body and extending around at least ¼ of a circumference of the external surface of the filter body, and having an opposite convex surface configured to conform with the inner wall of the body lumen.

In one embodiment, each wall contact has a longitudinal length dimensioned to inhibit the filter from migrating within the body lumen of the subject. As such, the longitudinal length of the wall contact has a dimension from about 0 mm to about 50 mm, from about 0.001 to about 25 mm, and/or about 0.1 mm to about 10 mm.

In one embodiment, the wall contact is dimensioned so as to inhibit endothelial cell ingrowth into the apertures.

In one embodiment, the wall contact can be formed from any polymeric material disclosed herein or other similar polymers.

In one embodiment, the wall contact is formed from a biodegradable polymer selected from the group consisting of a natural polymer, synthetic polymer, polysaccharide, starch, cellulose, protein, gelatin, casein, polyesters, polyhydroxyalkanoates, lignin, shellac, natural rubber, polyalkylene esters, polylactic acids, polylactides, polyglycolic acids, polyglycolides, polyamide esters, polyvinyl esters, polyvinyl alcohols, polyanhydrides, polyesters, salts thereof, copolymers thereof, and combinations thereof.

In one embodiment, the wall contact is shaped and dimensioned as a coating applied over the external surface of the filter. This can include the coating being disposed and/or extending through the apertures of the filter. Also, this can include the coating being sprayed, inkjetted, dipped, rolled, painted, or otherwise applied to the filter.

In one embodiment, the wall contact is shaped and dimensioned as a sleeve into which the filter is inserted. As such, the wall contact fits onto the filter similar to a sleeve.

In one embodiment, the wall contact can be coated with a biocompatible polymeric material as described herein. Such coatings can include hydrogels, hydrophilic and/or hydrophobic compounds, and polypeptides, proteins or amino acids or the like. Specific examples can include polyethylene glycols, polyvinylpyrrolidone (PVP), polyvinylalcohol (PVA), parylene, heparin, phosphorylcholine, polytetrafluorethylene (PTFE), or the like.

In one embodiment, the wall contact can be configured as a drug eluting wall contact. Such wall contacts are provided on the filter to facilitate the loading or delivery of beneficial agents or drugs, such as therapeutic agents, pharmaceuticals and radiation therapies.

Accordingly, the wall contact can contain a drug or beneficial agent to improve the use of the filter. Such drugs or beneficial agents can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial genes, genes, siRNA, antisense compounds, oligionucleotides, cell permeation enhancers, and combinations thereof.

VI. Method of Making Filters

Various different manufacturing techniques are well known and may be used for fabrication of the filters, braids, strut elements, and or wall contacts of the present invention. Generally, processes for preparing endoprostheses, such as stents or filters, can be used to prepare the filters of the present invention. The filter is formed such that the braids and/or strut elements cooperate so as to form apertures, which function as the pores in a filter. For example, the fastener holes in the filter can be formed from a hollow tube using a known technique, such as laser cutting, EDM, milling, chemical etching, hydrocutting, and the like. The filter can be prepared to include multiple layers or coatings deposited through a cladding process such as vapor deposition, electroplating, spraying, or similar processes. Once the generally tubular shape is formed, the tube can be shaped as described herein. Such shaping can be done before or after the forming the apertures that serve the function as a filter. Also, various other processes can be used such as those described below and or others known to those skilled in the art in light of the teaching contained herein.

In one embodiment, the filter can be fabricated from a sheet of suitable material, where the sheet is rolled or bent about a longitudinal axis into the desired tubular shape. Additionally, either before or after being rolled into a tube, the material can be shaped to include filter elements, fastener holes, and pores by being shaped with well-known techniques such as laser-cutting, milling, etching or the like. If desired, the lateral edges of the structure can be joined together, such as by welding or bonding, to form a closed tubular structure, or the lateral edges can remain unattached to form a coiled, rolled sheet or open tubular structure. Such fabrication techniques are described in more detail below and known to those skilled in the art.

In one embodiment, the present invention provides a method of manufacturing a filter having a wall contact for use in a body lumen of a subject. Such a method includes: forming a filter body including a plurality of filter elements interconnected together such that the filter body has a plurality of apertures disposed between and defined by the interconnected filter elements, the apertures extending from an external surface to an internal surface of the filter body and being dimensioned so as to inhibit a thrombus of a selected size from passing through the apertures and being dimensioned so as to allow blood components smaller than the selected size to pass through the apertures; forming at least one fastener hole in the filter body so as to extend from the external surface to the internal surface; inserting at least one fastener extending through the at least one fastener hole; and coupling at least one biodegradable wall contact to the external surface of the filter body by being coupled to the at least one fastener extending through the at least one fastener hole, the wall contact having an initial thickness dimension that is substantially orthogonal to central axis of the filter body and that separates the external surface from an inner wall of the body lumen.

In one embodiment, the method of manufacture includes at least one of the following: forming the wall contact so as to have a square to rectangular block cross section; forming the wall contact so as to have a square to rectangular block cross section having a long dimension that extends from the external surface of the filter body; forming the wall contact so as to have a square to rectangular block cross section having a convex surface coupled to the external surface of the filter body; forming the wall contact so as to have a square to rectangular block cross section having a concave surface coupled to the external surface of the filter body and an opposite convex surface configured to conform with the inner wall of the body lumen; forming the wall contact so as to have an arc-shaped cross section having a concave surface coupled to the external surface of the filter body and an opposite convex surface configured to conform with the inner wall of the body lumen; forming the wall contact so as to have an arc-shaped cross section having a concave surface coupled to the external surface of the filter body and an opposite convex surface configured to conform with the inner wall of the body lumen; or forming the wall contact so as to have an arc-shaped cross section having a concave surface coupled to the external surface of the filter body and extending around at least ¼ of a circumference of the external surface of the filter body, and having an opposite convex surface configured to conform with the inner wall of the body lumen.

In one embodiment, the method of manufacture further includes forming the wall contact so as to have a longitudinal length dimensioned to inhibit the filter from migrating within the body lumen of the subject.

In one embodiment, the method of manufacture further includes: forming the at least one fastener hole shaped as a keyway slot having a large portion and a narrow portion; and forming the at least one fastener to have a stem that fits through the narrow portion of the keyway slot and a head portion that fits through the large portion and that is larger than the narrow portion of the keyway slot.

A. Sintering

A method of making a filter can include sintering sinterable particles to provide a sintered article having the shape of the filter. The sintering can be conducted in molds that are in the shape of a general tube or in the shape of the filter. This can include molds that provide the fastener holes and/or apertures.

In one configuration, the sintered body can be obtained from a molded green body prepared by molding a mixture of sinterable particles with or without a binder into the shape of a filter or body intermediate. Sintering a molded green body that has the shape of a filter can provide a sintered body that can function as a filter with no or minimal further processing. Alternatively, after the green body has been formed in the mold and sintered into a hardened filter, the process can include shaping the sintered body with a stream of energy and/or matter in order to obtain a desired shape. This can include laser-cutting the apertures and/or forming the shape of the hourglass. Thus, sintering a green body in a mold can result in a filter that is either ready for use, or requires additional processing or finishing.

Additionally, the sintered body can be shaped into a filter as described herein. Also, the filter can be further processed after sintering and/or shaping such as by grinding, sanding, or the like to provide enhanced surface characteristics.

B. Drawing Concentric Tubes

In one configuration, a multilayered filter in accordance with the present invention can be prepared by a drawing process that draws two or more distinct concentric tubes into a single tube having two or more layers. Additionally, such a drawing process can combine multiple concentric tubes into a single multilayered tube. Alternatively, the different layers can function as the different portions, such as the large diameter ends and the tapered center. The drawing process can be configured to produce junctions separating adjacent layers or bonds that bond adjacent layers. As such, the sequentially-adjacent concentric tubes can be drawn together and progressively reduced in a cross-sectional profile until the desired size and residual clamping stress is attained.

Accordingly, a metallurgical bond can be prepared with elements of each sequentially-concentric tube diffusing together and bonding so as to form a strong metallurgical bond. Such a metallurgical bond can be achieved by applying significant pressure and heat to the tubes. As such, a metallurgical bond can form a diffusion layer at the interface between sequentially-adjacent concentric tubes (i.e., layers). The characteristics of these diffusion layers can be controlled by the proper heat treatment cycle. In part, this is because the heat treatment, temperature, and time of processing can control the rates of transfer of the diffusing elements that produce the diffusion layers. Also, the pressure at the interface between layers can be developed so as to result in the residual radial clamping stress in the tube after drawing.

In one example of this process, an outer tube of nitinol, a middle tube of tantalum, and an inner tube of nitinol can be arranged to form the composite structure. The multilayered material can be produced to result in bonding between the layers so as to achieve a residual clamping stress of at least about 50 p.s.i. Accordingly, the annealing process can be performed within a limited range of time and temperatures. For example, the lower limit can be at least about 1550° F. for at least six minutes, and the upper limit can be less than about 1850° F. for less than 15 minutes.

In another configuration, a metallic interleaf layer can be placed between separate tubes so as to bond the tubes together and form a multilayered material. The multiple tubes separated by the metallic interleaf layer can be drawn together and progressively reduced until the desired cross-sectional profile and residual clamping stress is attained, as described above. The drawn tubes can be heat-treated to form a diffusion bond between the separate layers. As such, the metallic interleaf layer can enhance the diffusion rate or type of diffusing atoms that are transported across a diffusion region between one layer and the interleaf layer.

In one configuration, a multilayered sheet can be prepared to have separate layers of different materials or the same material. For example, the multilayered sheet can have a top layer of nitinol, a middle layer of tantalum, and a bottom layer of Nitinol. The sheet can be prepared by metallurgically bonding the layers prior to a deep drawing process, which is well known in the art. During the deep drawing process, the sheet can be placed over a die and forced into the die, such as by a punch or the like. A tube having a closed end and a defined wall thickness can be formed in the die. This process can be repeated using a series of dies that have progressively decreasing diameters until a multilayered tube is formed having the desired diameter and wall thickness. For certain material combinations, intermediate heat treatments can be performed between the progressive drawing operations to form a multilayered material that is resistant to delaminating. Once a multilayered tube of desired thickness and dimensions has been formed, the closed end and the curved edges can be cut off. Then, the tube can be heat treated, as described above, until proper inter-metallic bonds are formed between the layers.

C. Shaping

Accordingly, a filter material can be shaped by various methods as described in more detail below. This can include shaping the apertures and fastener holes into the filter body. Such shaping techniques can utilize streams of energy and/or streams of matter in order to impart shapes into the filter material. The streams of energy include photons, electromagnetic radiation, atomic, and sub-atomic materials, as described above. On the other hand, the streams of matter are considered to include materials larger than atomic scale particles, and can be microscopic or macroscopic in size. In any event, the shaping can be designed to direct a stream of energy or a stream of matter at the filter material to form an endoprosthetic element and/or holes therein.

In one configuration, a stream of energy can cut, shape, and/or form a tube into a filter by generating heat at the site where the stream intersects the material, as is well known in the art. The thermal interaction can elevate the local temperature to a point, which can cut, melt, shape, and/or vaporize portions of the filter material from the rest of the material.

Accordingly, one configuration of the stream-cutting apparatus can operate and shape the filter material by thermal interactions. As such, any of the thermal processes described herein can be used for thermal-cutting. For example, such thermal interactions can arise from laser beam treatment, laser beam machining, electron beam machining, electrical discharge machining, ion beam machining, and plasma beam machining.

In one configuration, by knowing the thermal properties of the filter material, precise energy requirements can be calculated so that the thermal beam provides the appropriate or minimum energy for melting and/or vaporizing the material without significantly melting undesirable portions of the material. For example, laser beams are a common form of a stream of energy that can be used to shape the filter material. Additionally, there are instances where a laser is preferred over all other cutting techniques because of the nature of the resulting filter as well as the characteristics of the filter material.

In one configuration, a filter may be manufactured as described herein using a femtosecond laser. A femtosecond laser may be desirable in producing an endoprosthesis in accordance with the multilayered composite structure of the present invention because it produces a smaller heat influence zone (HIZ) or heat affected zone (HAZ) compared to other lasers, or it can substantially eliminate the HIZ or HAZ. In comparison, cutting a filter using known methods can result in the tubular material being melted away, and thereby forming the pattern in the tubular member. Such melting can result in embrittlement of some materials due to oxygen uptake into the HIZ.

In one configuration, electrical discharge machining is used to shape filter material and/or form holes in the material as desired. As such, electrical discharge machining can be capable of cutting all types of conductive materials such as exotic metal including titanium, hastaloy, kovar, hard tool steels, carbides, and the like. In electrical discharge, the main interaction between the stream of energy and the filter material is thermal, where heat is generated by producing electrical discharges. This can lead to the filter material being removed by melting and evaporation. Some examples of electrical discharge machining include wire electron discharge machining, CNC-controlled electrical discharge machining, sinker electrical discharge machining, small hole discharge machining, and the like.

In another configuration, a charged particle beam can be used for shaping the filter material, wherein electron beams and ion beams exemplify charged particle beams. A charged particle beam is a group of electrically-charged particles that have approximately the same kinetic energy and move in approximately the same direction. Usually, the kinetic energies are much higher than the thermal energies of similar particles at ordinary temperatures. The high kinetic energy and the directionality of these charged beams can be useful for cutting and shaping of the green bodies, as described herein. Additionally, there are some instances where electron beams or ion beams are preferred over other cutting techniques.

In one configuration, a stream of chemical matter can be used in order to shape or form holes in the filter material. Chemical-jet milling, for example, provides selective and controlled material removal by jet and chemical action. As such, the process is similar to water-jet cutting, which is described in more detail below. In any event, chemical-jet milling can be useful for shaping various types of filter materials, which provides intricate shaping capabilities.

In another configuration, electrochemical shaping can be based on a controlled electrochemical dissolution process similar to chemical-jet milling a filter material. As such, the filter material can be attached to an electrical source in order to allow an electrical current to assist in the shaping.

In one configuration, hydro-cutting or water-jet cutting can be used to shape a filter material. Hydro-cutting is a water-jet technology that uses the high force and high pressure of a stream of water directed at the filter material in order to cut and shape the material as desired. Hydro-cutting can be preferred over some of the other stream-cutting technologies because it can be free of heat, flame, and chemical reactions, and can provide a precise cold shaping technique. Also, heated water with or without being doped with reactive chemicals can also be used. Hydro-cutting is particularly suitable for polymeric filters, but can be used for metal materials when combined with abrasive particles, as described below.

Additionally, hydro-cutting can be enhanced by the introduction of particulate materials into the water feed line. As such, some hydro-cutting techniques utilize garnet or other rigid and strong materials in order to apply an abrasive cutting force along with the force applied by the water itself. Also, the hydro-cutting process in the present invention can be used with or without inclusion of such abrasives.

Additionally, one of the benefits of hydro-cutting is the ability to reutilize and recycle the spent water-jet material. As such, the filter material can be easily separated from the spent water, thereby enabling the recycling and reuse of the water during the hydro-cutting process.

In one configuration, sandblasting, which fits into the regime of stream of matter cutting, can be used to shape a filter material by projecting a high energy stream of sand particles at the material. Sandblasting cuts materials in a manner similar to hydro-cutting, especially when the water-jet is doped with abrasive particulates. Additionally, various other particulate streams other than sand can be used in the stream-cutting techniques and machinery.

D. Heat Setting

In general, a filter may be manufactured into the free recovery shape through heat setting a superelastic material. If the superelastic filter is required for a particular application, such as inside of a superficial femoral artery, the large end of the filter may need to be as large as about 10 millimeters. Increasing the diameter of the large end of the filter and/or forming the conical or funnel shape can be a gradual process with individual steps often being expansions of only 1 millimeter. This allows the diameter of the large end portion and the enlargement of the conical portion to be gradually increased in size from the center point or the center conduit of the filter. The number of steps that are repeated can be up to and over 10 steps. Therefore, in the case of having a superelastic nitinol hollow tube with an inner diameter of 1.3 millimeters, after about 8 steps, the diameter of the large end portions may be around 10 millimeters, which is sufficient for most intraluminal endoprosthestic applications within the human body. The beginning diameter and the final diameter of the large end portions may be smaller or larger depending upon the desired final diameter that a filter needs to be for a particular application.

When the filter is configured to have the final diameter necessary (e.g., diameter of large end portion) for its particular application, the filter may then be heated according to the method of the present invention in order to provide the filter shape.

In one embodiment, a nickel titanium or nitinol filter can be heat set. Heat setting is a process whereby the nitinol, or other superelastic material, is heated to a temperature far above its austenitic finish temperature in a desired shape, (e.g., large end portions, tapered central portion, cones, filters, hourglass and/or the like), followed by water quenching. A filter may be deformed at the heat set temperature into a new shape, such as being transformed from a cylindrical shape to the filter shape. When the filter is cooled so it is in the martensitic form, the filter may be deformed into the delivery configuration. When the deformed, martensitic filter is introduced into a body lumen, for example, the temperature of the filter rises to (and above) the austenitic finish temperature and the filter will then reform to the heat set filter shape.

The temperature and the time of heating of the filter depend upon the composition of the superelastic metal and the particular application of filter. For example, a nitinol superelastic metal alloy having a composition of 49% nickel and 51% titanium can have different characteristics than a nitinol superelastic metal alloy having a binary composition of nickel and titanium. Using a standard superelastic nitinol (55.3-56.3 wt. % Ni), a temperature of about 500 degrees Celsius for about 30 seconds or more is preferable to configure the filter into the hourglass shape. A useable range of temperatures for standard superelastic nitinol metals is from about 400 to about 600 degrees Celsius for greater than about 30 seconds. Temperature ranges and times of heat treatment also change when strengthening elements such as Cr are added.

E. Forming Wall Contact

Generally, the wall contacts can be prepared by any well known process for preparing polymeric members. Examples of such a process include the following: shaping a block of the polymer into the shape of the wall contact; molding the wall contact from the polymer; injection molding the wall contact; stamping the wall contact from a polymeric sheet; dip coating the polymer onto the filter so as to form a wall contact; and other similar processes for preparing polymeric members. Processes for preparing polymeric members are well known in the art.

In one embodiment, the method of manufacture includes at least one of the following: forming the wall contact so as to have a square to rectangular block cross section; forming the wall contact so as to have a square to rectangular block cross section having a long dimension that extends from the external surface of the filter body; forming the wall contact so as to have a square to rectangular block cross section having a convex surface coupled to the external surface of the filter body; forming the wall contact so as to have a square to rectangular block cross section having a concave surface coupled to the external surface of the filter body and an opposite convex surface configured to conform with the inner wall of the body lumen forming the wall contact so as to have an arc-shaped cross section having a concave surface coupled to the external surface of the filter body and an opposite convex surface configured to conform with the inner wall of the body lumen; or forming the wall contact so as to have an arc-shaped cross section having a concave surface coupled to the external surface of the filter body and extending around at least ¼ of a circumference of the external surface of the filter body, and having an opposite convex surface configured to conform with the inner wall of the body lumen.

F. Coupling Wall Contact with Filter

The wall contact can be permanently or removably coupled to the filter. There are a variety of processes for attaching a first member to a second member of a medical device that are well known in the art. This can include the use of fasteners, adhesives, coatings, couplings and the like.

In the instance of a wall contact in the form of a coating, the coating can be applied to the filter. Usually, coatings are not removable except when the biodegradable polymer is fully depleted. As such, the coating can be formed onto the filter by being sprayed, inkjetted, dipped, rolled, painted, or otherwise applied to the filter.

In the instance of a wall contact in the form of a sleeve, the sleeve is preformed and the filter is inserted therein. The sleeve can be form-fitted to the filter and/or adhesives can be used to secure the sleeve to the filter.

In the instance the wall contact is a polymeric member, the fasteners of the present invention can be used to removably or permanently couple the wall contact to the filter. The fastener and wall contact can form a fastener system substantially similar to those used in the medical arts to attach one medical component to another medical component. For example, the fastener system can include the wall contact having a bolt-like protrusion extending through the fastener hold of the filter with a nut securing the wall contact to the filter by being fitted onto the bolt-like protrusion. In another example, the fastener is a nail-like structure integrated with the wall contact or formed therewith. In yet another example, the fastener is a screw that fits through the fastener hole and into the wall contact, where the screw head is larger than at least a portion of the fastener hole. In still yet another example, the wall contact includes a recess, such as a threaded recess, to receive the fastener.

Additionally, the wall contact can be removably coupled to the filter by forming the filter to have at least one keyway slot shape and to form the fastener to have a stem that fits through the narrow portion of the keyway slot and a head portion that fits through the large portion and that is larger than the narrow portion of the keyway slot. As such, the head portion can be inserted through the large portion of the keyway slot until the stem is disposed therein. The stem is then slid into the narrow portion of the keyway slot such that the head portion is disposed on the internal surface of the filter.

G. Additional Processing

An additional step of passivation can be performed during the manufacturing stage of the filter in order to form a homogeneous oxide layer for corrosion-resistance. The passivation process may be performed prior to installation of the markers in accordance with the present invention or it may be performed after installation of the radiopaque markers. Alternatively, multiple passivation processes may be performed, once prior to application of the markers, and again after insertion of the markers.

As originally shaped and/or fabricated, the filter can correspond to its delivery configuration, to a deployed configuration, or to a configuration therebetween. The filter can be fabricated with a configuration at least slightly larger than the delivery configuration. In this manner, the filter can be crimped or otherwise compressed into its delivery configuration in a corresponding delivery device.

In another configuration, the filter can be originally fabricated from a tube having a diameter corresponding to the deployed configuration. The filter can be designed to match the target vessel in which the filter is to be deployed. For example, a stent can be provided with an outer diameter in the deployed configuration ranging from about 1 mm for neurological vessels to about 25 mm for the aorta. Similarly, a stent can be provided with a length ranging from about 5 mm to about 200 mm. Variations of these dimensions will be understood in the art based upon the intended application or indication for the filter.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A filter for use in a body lumen of a subject, the filter comprising:
an elongate filter body having a funnel-shaped filter portion, a plurality of filter elements interconnected so as to form said filter body with a plurality of apertures disposed between and defined by said interconnected filter elements, said substantially funnel-shaped portion being differently configured from a remainder of said elongate filter body and including a plurality of spaced apart, independent radial filter elements and a plurality of circular filter elements, said plurality of spaced apart radial filter elements spiraling from a small end of said substantially funnel-shaped portion to a large end of said substantially funnel-shaped portion, adjacent spaced apart radial filter elements forming a filter aperture extending from said small end to said large end and having an increasing diameter from said small end to said large end, said plurality of circular filter elements being of increasing diameter from said small end to said large end and being perpendicular to a longitudinal axis of said filter body, said plurality of circular filter elements cooperating with said plurality of spaced apart radial filter elements along the lengths of said plurality of spaced apart radial filter elements to form a plurality of reduced filter apertures from said plurality of filter apertures, said reduced filter apertures extending from an external surface to an internal surface of said filter body and being dimensioned so as to inhibit a thrombus of a selected size from passing through said apertures and being dimensioned so as to allow blood components smaller than the selected size to pass through said apertures; and
at least one biodegradable wall contact coupled to at least one of said filter elements on said external surface of said filter body, said wall contact having an initial thickness dimension that is substantially orthogonal to central axis of said filter body and that separates said external surface from an inner wall of said body lumen.

2. The filter as in claim 1, where said filter body is a substantially hourglass shape with a conduit having a narrow median portion being dimensioned so as to inhibit the thrombus of the selected size from passing therethrough.

3. The filter as in claim 2, said at least one wall contact further comprises at least one of the following:
a rectangular block cross section;
a rectangular block cross section having a long dimension that extends from said external surface of said filter body; or
a rectangular block cross section having a convex surface coupled to said external surface of said filter body.

4. The filter as in claim 3, wherein said at least one wall contact has a longitudinal length dimensioned to inhibit said filter from migrating within the body lumen of the subject.

5. The filter as in claim 4, wherein said longitudinal length of said at least one wall contact has a dimension from about 0 mm to about 50 mm.

6. The filter as in claim 4, wherein said at least one wall contact is dimensioned so as to inhibit endothelial cell ingrowth into said apertures.

7. The filter as in claim 1, further comprising at least one of the following:
said at least one wall contact being coated onto said external surface so as to extend into at least a portion of said plurality of apertures;
at least one filter element defining a hole with a portion of said wall contact extending therethrough;
at least one filter element defining a hole with a fastener extending therethrough and coupling with said at least one wall contact;
at least one filter element defining a hole shaped as a keyway slot and a portion of said wall contact extending therethrough;
at least one filter element defining a hole shaped as a keyway slot with a fastener extending therethrough and coupling with said at least one wall contact;
at least one filter element defining a hole shaped as a keyway slot having a large portion and a narrow portion and a portion of said wall contact extending therethrough, said portion of said wall contact having a stem that fits through said narrow portion of said keyway slot and a head portion that fits through said large portion and that is larger than said narrow portion of said keyway slot; or
at least one filter element defining a hole shaped as a keyway slot having a large portion and a narrow portion with a fastener extending therethrough and coupling with said at least one wall contact, said fastener having a stem that fits through said narrow portion of said keyway slot and a head portion that fits through said large portion and that is larger than said narrow portion of said keyway slot.

8. The filter as in claim 1, further comprising at least one fastener coupling said at least one wall contact to said external surface of said filter body.

9. The filter as in claim 1, wherein said biodegradable polymer is selected from the group consisting of a natural polymer, synthetic polymer, polysaccharide, starch, cellulose, protein, gelatin, casein, polyesters, polyhydroxyalkanoates, lignin, shellac, natural rubber, polyalkylene esters, polylactic acids, polylactides, polyglycolic acids, polyglycolides, polyamide esters, polyvinyl esters, polyvinyl alcohols, polyanhydrides, polyesters, salts thereof, copolymers thereof, and combinations thereof.

10. The filter as in claim 1, further comprising:
said wall contact having an arc-shaped cross section having a concave surface coupled to said external surface of said filter body and an opposite convex surface configured to conform with the inner wall of the body lumen and is dimensioned so as to inhibit endothelial cell ingrowth into said apertures; and
at least one filter element defining a hole shaped as a keyway slot having a large portion and a narrow portion with a fastener extending therethrough and coupling with said at least one wall contact, said fastener having a stem that fits through said narrow portion of said keyway slot and a head portion that fits through said large portion and that is larger than said narrow portion of said keyway slot.

11. A filter for use in a body lumen of a subject, the filter comprising:
a filter body having a substantially hourglass configuration with a first body portion, a first substantially funnel-shaped portion, a median body portion, a second substantially funnel-shaped portion, and a second body portion, a plurality of filter elements interconnected so as to form the first body portion, the medial body portion and the second body portion with a plurality of apertures disposed between and defined by said interconnected filter elements, said first substantially funnel-shaped portion and said second substantially funnel-shaped portion each including a plurality of spiraling, spaced apart filter elements and a plurality of circular filter elements, said plurality of spiraling, spaced apart filter elements spiraling from a small end of each said first substantially funnel-shaped portion and said second substantially funnel-shaped portion to a large end of each said first substantially funnel-shaped portion and said second substantially funnel-shaped portion, adjacent spaced apart radial filter elements forming a filter aperture extending from said small end to said large end and having an increasing diameter from said small end to said large end, said plurality of circular filter elements being of increasing diameter from said small end to said large end and being perpendicular to a longitudinal axis of said filter body, said plurality of circular filter elements cooperating with said plurality of spiraling, spaced apart radial filter elements along the lengths of said plurality of spaced apart radial filter elements to form a plurality of reduced filter apertures from said plurality of filter apertures, said reduced filter apertures extending from an external surface to an internal surface of said filter body and being dimensioned so as to inhibit a thrombus of a selected size from passing through said apertures and being dimensioned so as to allow blood components smaller than the selected size to pass through said apertures;
at least one filter element defining at least one fastener hole extending from said external surface to said internal surface;
at least one fastener extending through said at least one fastener hole; and
at least one biodegradable wall contact removably coupled to said at least one filter element on said external surface of said filter body by being coupled to said at least one fastener extending through said at least one fastener hole, said wall contact having an initial thickness dimension that is substantially orthogonal to central axis of said filter body and that separates said external surface from an inner wall of the body lumen.

12. The filter as in claim 11, wherein the median portion is dimensioned so as to inhibit the thrombus of the selected size from passing therethrough.

13. The filter as in claim 12, said at least one wall contact further comprising at least one of the following:
a rectangular block cross section;
a rectangular block cross section having a long dimension that extends from said external surface of said filter body; or
a rectangular block cross section having a convex surface coupled to said external surface of said filter body.

14. The filter as in claim 13, wherein said at least one wall contact has a longitudinal length dimensioned to inhibit said filter from migrating within the body lumen of the subject.

15. The filter as in claim 14, wherein said longitudinal length of said at least one wall contact has a dimension from about 0 mm to about 50 mm.

16. The filter as in claim 14, wherein said at least one wall contact is dimensioned so as to inhibit endothelial cell ingrowth into said apertures.

17. The filter as in claim 11, further comprising at least one of the following:
said at least one fastener hole being shaped as a keyway slot;
said at least one fastener hole being shaped as a keyway slot keyway slot with said at least one fastener extending therethrough and coupling with said at least one wall contact;
said at least one fastener hole being shaped as a keyway slot having a large portion and a narrow portion with said at least one fastener extending therethrough and coupling with said at least one wall contact, said fastener having a stem that fits through said narrow portion of said keyway slot and a head portion that fits through said large portion and that is larger than said narrow portion of said keyway slot.

18. The filter as in claim 11, wherein said at least one fastener is at least one of the following:
integrated with said at least one wall contact;
removably coupled with said at least one wall contact; or
a portion of said at least one wall contact.

19. The filter as in claim 11, wherein said biodegradable polymer is selected from the group consisting of a natural polymer, synthetic polymer, polysaccharide, starch, cellulose, protein, gelatin, casein, polyesters, polyhydroxyalkanoates, lignin, shellac, natural rubber, polyalkylene esters, polylactic acids, polylactides, polyglycolic acids, polyglycolides, polyamide esters, polyvinyl esters, polyvinyl alcohols, polyanhydrides, polyesters, salts thereof, copolymers thereof, and combinations thereof.

20. The filter as in claim 11, further comprising:
said wall contact having an arc-shaped cross section having a concave surface coupled to said external surface of said filter body and an opposite convex surface configured to conform with the inner wall of the body lumen and is dimensioned so as to inhibit endothelial cell ingrowth into said apertures; and
said at least one fastener hole shaped as a keyway slot having a large portion and a narrow portion with said at least one fastener extending therethrough and coupling with said at least one wall contact, said fastener having a stem that fits through said narrow portion of said keyway slot and a head portion that fits through said large portion and that is larger than said narrow portion of said keyway slot.

* * * * *